(12) United States Patent
Hodgkiss et al.

(10) Patent No.: US 10,788,483 B2
(45) Date of Patent: Sep. 29, 2020

(54) OPTIMIZATION METHOD OF A POLYNUCLEOTIDE SEQUENCE

(71) Applicant: Victoria Link Limited, Wellington (NZ)

(72) Inventors: Justin Hodgkiss, Wellington (NZ); Omar Alsager, Wellington (NZ); Shalen Kumar, Lower Hutt (NZ); Kenneth McNatty, Wellington (NZ)

(73) Assignee: Victoria Link Limited, Wellington (NZ)

( * ) Notice: Subject to any disclaimer, the term of this patent is extended or adjusted under 35 U.S.C. 154(b) by 0 days.

(21) Appl. No.: 15/311,500

(22) PCT Filed: May 15, 2015

(86) PCT No.: PCT/NZ2015/050061
§ 371 (c)(1),
(2) Date: Nov. 15, 2016

(87) PCT Pub. No.: WO2015/174863
PCT Pub. Date: Nov. 19, 2015

(65) Prior Publication Data
US 2017/0115281 A1 Apr. 27, 2017

(30) Foreign Application Priority Data

May 15, 2014 (NZ) ........................................ 624985
Oct. 30, 2014 (NZ) ........................................ 701471

(51) Int. Cl.
| | |
|---|---|
| *A61K 48/00* | (2006.01) |
| *C07H 21/04* | (2006.01) |
| *G01N 33/53* | (2006.01) |
| *C12N 15/115* | (2010.01) |
| *G01N 21/78* | (2006.01) |
| *G01N 33/74* | (2006.01) |
| *G01N 21/75* | (2006.01) |

(52) U.S. Cl.
CPC ....... *G01N 33/5308* (2013.01); *C12N 15/115* (2013.01); *G01N 21/78* (2013.01); *G01N 33/743* (2013.01); *C12N 2310/16* (2013.01); *C12N 2310/351* (2013.01); *C12N 2320/10* (2013.01); *G01N 2021/757* (2013.01)

(58) Field of Classification Search
CPC ............................ A61K 2300/00; A61K 45/06
See application file for complete search history.

(56) References Cited

U.S. PATENT DOCUMENTS

2009/0197261 A1* 8/2009 Lu .......................... B82Y 15/00
435/6.11
2016/0017332 A1* 1/2016 Berzal Herranz ... C12N 15/115
514/44 R

OTHER PUBLICATIONS

Levy-Nissenbaum et al. (Trends in Biotechnology, vol. 26, No. 8, 2008, pp. 442-449).*
Liu et al. (Nature Protocols, vol. 1, No. 1, 2006, pp. 246-252).*
Schoukroun-Barnes et al. (Analytical Chemistry, 2014, vol. 86, pp. 1131-1137, published Dec. 30, 2013).*
International Preliminary Report on Patentability for Application No. PCT/NZ2015/05006 dated Sep. 5, 2016.
Alizadeh et al., A Review on Gold Nanoparticles Aggregation and Its Applications. Journal of Chemistry. Jul. 2019; 1-52.
Pamies et al., Aggregation behaviour of gold nanoparticles in saline aqueous media. J Nanopart Res. Apr. 1, 2014; 16:2376. doi: 10.1007/s11051-014-2376-4.
Singh et al., Effect of size and charge asymmetry on aggregation kinetics of oppositely charged nanoparticles. Sci Rep. Mar. 6, 2019;9(1):3762. doi: 10.1038/s41598-019-40379-y.
Tyagi et al., A Facile pH Controlled Citrate-Based Reduction Method for Gold Nanoparticle Synthesis at Room Temperature. Nanoscale Res Lett. Dec. 2016;11(1):362. doi: 10.1186/s11671016-1576-5. Epub Aug. 15, 2016.
Beyer et al., Design Variations for an Aptamer-Based DNA Nanodevice. J Biomedical Nanotechnology. 2005;1:96-101.
Schoukroun-Barnes et al., Enhancing the analytical performance of electrochemical RNA aptamer-based sensors for sensitive detection of aminoglycoside antibiotics. Anal Chem. Jan. 21, 2014;86(2):1131-7. doi:10.1021/ac4029054. Epub Jan. 9, 2014. Erratum in: Anal Chem. May 20, 2014;86(10):5188. Wagan, Samuillah [corrected to Wagan, Samiullah].
Zhang et al., Surface science of DNA adsorption onto citrate-capped gold nanoparticles. Langmuir. Feb. 28, 2012;28(8):3896-902. doi:10.1021/la205036p. Epub Feb. 13, 2012.
Zhao et al., DNA aptamer folding on gold nanoparticles: from colloid chemistry to biosensors. J Am Chem Soc. Mar. 19, 2008;130(11):3610-8. doi: 10.1021/ja710241b. Epub Feb. 23, 2008.

* cited by examiner

*Primary Examiner* — Amy H Bowman
(74) *Attorney, Agent, or Firm* — Wolf, Greenfield & Sacks, P.C.

(57) ABSTRACT

The present invention provides for a method of optimisation of a polynucleotide sequence for use in an aptamer based assay, comprising adding additional bases to the ligand binding domain. The invention also covers methods of detecting target molecules in a sample using 5 optimised polynucleotide sequences in a suitable detection assay.

6 Claims, 14 Drawing Sheets
Specification includes a Sequence Listing.

A

OPTIMIZATION METHOD OF A POLYNUCLEOTIDE SEQUENCE

RELATED APPLICATIONS

This application is a U.S. National Stage patent application based on International Application PCT/NZ2015/050061, filed May 15, 2015, which claims priority to New Zealand Patent Application No. 624985, filed May 15, 2014 and New Zealand Patent Application No. 701471, filed Oct. 30, 2014, which are incorporated herein by reference in their entirety.

This invention relates to the optimisation of polynucleotide sequences, uses of the polynucleotide sequences in methods detecting small molecules and/or other target substrates in samples using nanoparticles coated with the polynucleotide sequence.

INTRODUCTION

As part of environment testing there is an on-going need for methods of rapidly detecting and quantifying the presence of target substrates. For example, target small molecules such as endocrine-disrupting compounds and hormones are often found as contaminants in the environment. Such contaminants can be found in waterways, soils, biological samples, including both plant and animals, as environmental pollutants from residential, agricultural, commercial and/or industrial applications.

It is known, in some cases, that small molecular weight compounds, such as those indicated herein, together with their metabolites and/or synthetically modified variants pose a threat to the health of human and wildlife populations by mimicking the activity of endogenous hormones, such as oestrogens. These molecules may act by blocking, mimicking, stimulating or inhibiting the production and function of natural hormones. The organic residues that mimic these endogenous steroidal hormones, and metabolites are lipid soluble, thus have the ability to bio-accumulate in living systems of mammals and marine species. Evidence of this has been identified in human blood plasma, breast milk, foetal tissues and biological fluids [Allmyr et al., Anal. Chem., 78: 6542-6546, 2006; Hileman, Chemical and Engineering News, 85: 31-33, 2007; Van-Pelt et al. Endocrinology, 140: 478-483, 2001; Skakkebaek et al., Human Reproduction 16: 972-978, 2001; Vandenberg et al., Endocrine Reviews, 33(3): 2012] Therefore, there is a need for new methods for easy detection of these small molecules.

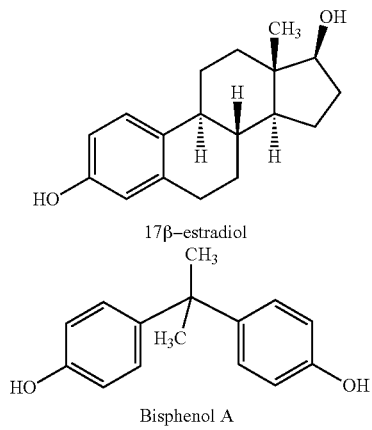

17β–estradiol

Bisphenol A

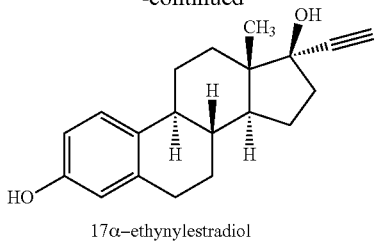

17α–ethynylestradiol

More conventional methodologies and techniques that are often used for the detection of small compounds include High Performance Liquid Chromatography (HPLC) or Gas Chromatography coupled with Mass Spectrometry (GCMS). These techniques are very useful for this purpose; however, the analyses can be complicated to perform and can take a long period of time to complete. Furthermore, sample concentration is often required for standard chromatographic techniques and cannot be carried out in situ [Campbell, C. G., et al., 2006, Chemosphere, 65, 1265-80]. Consequently, these techniques cannot be performed on site, they require specialised equipment and trained operators, and do not provide for a rapid assessment of the sample.

Aptamers are single-stranded nucleic acids (ssRNA, ssDNA), which unlike traditional nucleic acids, possess unique binding characteristics to specific targets with high affinity and specificity analogous to antibodies [Tuerk, C. Gold, L., Science, 1990, 249(4968), 505-510; Ellington, A. D., Szostak, J. W., Nature, 1990, 346(6287), 818-822.] Aptamers are typically isolated in vitro from combinatorial oligonucleotide libraries, typically containing $10^{12}$ to $10^{15}$ oligonucleotides, and are chemically synthesised by a process known as SELEX. The oligonucleotides are subjected to a selection process for their ability to bind a specified target and over a number of selection rounds (typically 8-16 rounds); the most specific nucleic acid sequences are isolated. Depending on the techniques used in SELEX, the process might take from days to months [Cho, E. J., Lee, J. W., Ellington, A. D., Ann. Rev. Anal. Chem., 2009, 2(1), 241-264; Ellington, A. D., Ann. Rev. Anal. Chem., 2009, 2(1), 241-264].

Aptamers have been generated for a wide range of targets, ranging from ions to entire cells. The benefits of synthetically evolved DNA aptamers, [Tuerk, C. Gold, L., Science, 1990, 249(4968), 505-510; Ellington, A. D., Szostak, J. W., Nature, 1990, 346(6287), 818-822], led to their widespread use as recognition elements in sensors [McKeague, M., Derosa, M. C., 2012. J. Nucleic Acids, 2012, 748913]. DNA aptamers are generated from a random core sequence, and also flanking primers which can later be used for amplification by polymerase chain reaction [McKeague, M., Derosa, M. C., 2012. J. Nucleic Acids, 2012, 748913]. The use of an in vitro process enables the generation and selection of aptamers that can bind toxic targets, which are not possible by immunologically initiated recognition elements, such as antibodies. The small size of aptamers (generally <3 nm in a coiled conformation) also makes them more readily applicable to surface-based aqueous sensing purposes in comparison to antibodies (approximately >10 nm in size) [Song, S., at al., Trends in Analytical Chemistry, 2008, 27(2), 108-117].

Baker et al., [Olowu, R. A.; Arotiba, O.; Maliu, S. N.; Waryo, T. T.; Baker, P.; Iwouoha, E., Sensors, 2010, 10, 9872] have previously shown that electrochemical DNA aptasensors developed from poly(3,4-ethylenedioxythiophene) (PEDOT) doped with gold nanoparticles (AuNP) have high affinity for the detection of 17β-estradiol. The PEDOT-AuNP are synthesised for the immobilisation of 17β-estradiol. This PEDOT-AuNP is able to reliably detect 17β-estradiol in the range of 0.1 nM-100 nM, with a detection limit of 0.02 nM.

In addition, Baker et al. [Olowu, R. A., Ndangili, P. M., Baleg, A. A, Ikpo, C. O., Njomo, N., Baker, P, Iwuoha, E., *Int. J. Electrochem. Sci.,* 2011, 6, 1686] have also prepared and shown an aptamer biosensor developed from a dendritic first generation poly(propyleneimine)-polythiophene copolymer (shown below)-functionalised gold electrode via biotin-avidin interaction in the determination of endocrine disrupting compounds, especially 17β-estradiol.

Many small molecule aptasensors have been developed with original primers retained [Alsager, O. A, Kumar, S., Willmott, G. R., McNatty, K. P., Hodgkiss, J. M., Biosens. *Bioelectron.* 57C, 2014, 262-268; Kim, Y. S., Jung, H. S., Matsuura, T., Lee, H. Y., Kawai, T., Gu, M. B., *Biosens. Bioelectron.,* 2007, 22, 2525-31]. In several instances, sequences have been modified through insertions or deletions outside of the core region but without noticeable reductions in the aptamer affinity for the target molecule [Cekan, P., Jonsson, E. O., Sigurdsson, S. T., 2009, *Nucleic Acids Res.,* 37, 3990-5; Huizenga, D. E., Szostak, J. W., 1995, *Biochemistry,* 34, 656-65].

However, other aptasensors have refined the original sequences, and shown that flanking sequences including the

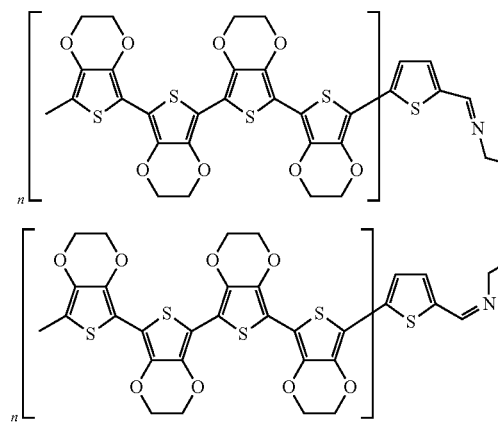
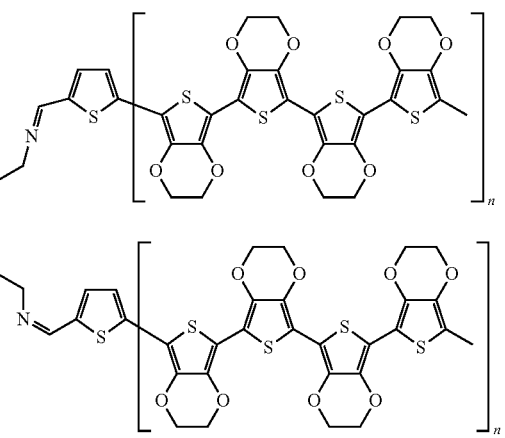

The sensor platform and aptasensor were investigated using techniques such as scanning electron microscopy, Fourier transform infrared spectroscopy, electrochemical impedance spectroscopy, cyclic voltammetry and square wave voltammetry. The authors report that the response in the detection of 17β-estradiol was measured using square wave voltammetry with a linear range of the sensor of 0.1 to 100 nM. In addition, this particular aptamer is specific only to 17β-estradiol.

Lee and Gu et al. [Kim, Y. S., Jung, H. S., Matsuura, T., Lee, H. Y., Kawai, T., Gu, M. B. *Biosensors and Bioelectronics,* 2007, 22, 2525] report the synthesis and use of ssDNA aptamer based electrochemical biosensors by immobilisation of the ssDNA aptamer on a gold electrode chip in the detection of 17β-estradiol. The detection levels of 17β-estradiol are reported to be in the range of from 1000 to 0.1 nM. However, the authors report at lower concentrations, in the range of 0.01 nM to 0.001 nM, their measurements may not be related to the binding of the aptamer to the substrate which makes this particular method unreliable.

US 2012/0088232 teaches a method for the detection of target molecules in patient samples at a point of care location using a point of care lateral flow device. The point-of-care lateral flow device specifically detects cancer markers and proteins, in particular p-glucoprotein (Pgp), by utilising aptamers that have been labelled with appropriate tags such as fluorophores. The aptamers are conjugated to solid supports, such as nanoparticles, and the presence of the target substrate molecules are quantified using techniques, including dynamic light scattering. In this case, dynamic light scattering measures increases in particle sizes associated with aptamer-substrate complex formation.

primers can potentially interfere with ligand binding. For example, in the detection of acetamiprid, the 91-mer aptamer has a $K_D$ of 498 nM. The aptamer is truncated to the 20-mer stem loop region and achieves detection levels of 5 nM in soil samples when applied in a colorimetric assay. [He, J., Liu, Y., Fan, M., Liu, X., 2011, *J. Agric. Food Chem.,* 59, 1582-6 and Shi, H., Zhao, G., Liu, M., Fan, L., Cao, T., *J. Hazard. Mater.,* 2013, 260, 754-761].

Similarly, bisphenol A aptasensors achieve low detection levels on reduction from a 106-mer aptamer ($K_D$ 8.3 nM) for the parent, to 1.2 pM and 400 pM for the reduced aptamer, in electrochemical and colorimetric sensors, respectively [Jo, M., Ahn, J.-Y., Lee, J., Lee, S., Hong, S. W., Yoo, J.-W., Kang, J., Dua, P., Lee, D.-K., Hong, S., Kim, S., 2011, *Oligonucleotides* 21, 85-91].

In the instance of the Ochratoxin A aptamer, more complicated effects are implied: affinity was drastically diminished upon removing both primers from the parent 61-mer ($K_D$ of 640 μM vs. 360 nM). However, more selective deletion results in an enhanced $K_D$ of 200 nM [Cruz-Aguado, J. a, Penner, G., 2008, *J. Agric. Food Chem.,* 56, 10456-61].

To date, the prior art focuses on the preparation of high affinity aptamers by reduction of the polynucleotide sequence to provide a sequence that essentially consists of the ligand binding domain (LBD). This approach assumes that sequences in excess of the LBD are redundant and are not required for effective small molecule and/or other target substrate binding and that reducing the sequence to the LBC will provide the best sequence for an aptamer based assay. This approach does not consider the issue of whether flanking sequences and excess nucleotide bases that are not directly involved in the ligand binding domain are required for the adsorption of the aptamer to a nanoparticle, microparticle or quantum dot in a colorimetric assay.

There is therefore a need for methodology to provide for a aptamer sequence with a good selectivity for use in a convenient, quick and simple method for the detection and quantification of small target molecules and/or other target substrates, especially in the area of environmental and contaminant testing.

There is therefore a need to provide and/or optimise polynucleotide (aptamer) sequences that provide accurate and sensitive results for any given assay.

It therefore is an object of the present invention to provide a highly effective method for small molecules and/or other target substrate detection in an assay using aptamers, or to at least provide the public with a useful alternative.

The method of the present invention is useful for providing high affinity aptamers in the detection of small molecules and/or other target substrate in a sample by using an aptamer coated NP to detect the presence of small molecules and/or other target substrate in a sample using an assay.

Any discussion of the prior art throughout the specification should in no way be considered as an admission that such prior art is widely known or forms part of the common general knowledge in the field.

SUMMARY OF THE INVENTION

The present inventors have advantageously and surprisingly developed a simple and reliable method for optimising a polynucleotide sequence for use in a given assay.

The present invention shows that the performance of the aptamer in the detection of target small molecules and/or other target substrates in a nanoparticle based assay is not only dependent on the binding affinity to the target substrate, but also that signal transduction and/or aptamer dissociation from the nanoparticles is very important and the aptamer sequence needs to be optimised to account for all of these variables.

The invention provides for optimisation of a polynucleotide sequence (aptamer) for use in an assay. It is required that the polynucleotide sequence comprises nucleotide bases in addition to the ligand binding domain wherein the additional nucleotide bases are selected to provide optimal signal transduction. Particularly, the optimisation of a polynucleotide sequence find use in a colorimetric aggregative aptasensor for the detection of small molecules and/or other target substrates. The present methodology provides detection limits to the pM range that show excellent selectivity for small target molecules and/or other target substrates

STATEMENTS OF INVENTION

In a first aspect, the present invention provides for a method of optimisation of a polynucleotide sequence for use in an assay, wherein the polynucleotide sequence comprises nucleotide bases in addition to the ligand binding domain, and the additional nucleotide bases are selected to provide optimal signal transduction.

In an embodiment of the first aspect, the polynucleotide is an aptamer. Preferably, the aptamer is selected from ssDNA and RNA. Most preferably, the aptamer is ssDNA.

In an embodiment of the first aspect, the additional nucleotide bases are situated at an end selected from the 5' end, the 3' end, or the 5' and 3' ends of the polynucleotide sequence.

In an embodiment of the first aspect, the method further comprises comparing two or more polynucleotide sequences, wherein at least one polynucleotide sequence has one or more additional nucleotide bases in addition to the ligand binding domain, and selecting a preferred polynucleotide sequence based on optimal sensitivity toward the small target molecule and/or other target substrates in an assay.

In another embodiment of the first aspect, the additional nucleotide bases comprise from 1 to 10 nucleotide bases at the selected end or ends. Preferably, the additional nucleotide bases comprise from 2 to 8 additional nucleotide bases at the selected end or ends. Most preferably, the additional nucleotide bases comprise from 4 to 7 nucleotide bases at the selected end or ends. The additional nucleotide bases may be selected from 1, 2, 3, 4, 5, 6, 7, 8, 9 and 10 nucleotide bases.

In another embodiment of the first aspect, the additional nucleotide bases comprise from 1 to 10 nucleotide bases at the selected end or ends. Preferably, the additional nucleotide bases comprise from 2 to 8 additional nucleotide bases at the selected end or ends. Most preferably, the additional nucleotide bases comprise from 4 to 7 nucleotide bases at the selected end or ends. The additional nucleotide bases may be selected from 1, 2, 3, 4, 5, 6, 7, 8, 9 and 10 nucleotide bases at the 3' end and/or 1, 2, 3, 4, 5, 6, 7, 8, 9 and 10 nucleotide bases at the 5' end.

In another embodiment of the first aspect, the additional nucleotide bases are sufficient to allow binding of the polynucleotide sequence to the nanoparticle together with binding to the small target molecules and/or other target substrates.

In an embodiment of the first aspect, the additional nucleotide(s) provide optimal signal transduction.

In an embodiment of the first aspect, the assay is selected from a nanoparticle assay, an aptamer assay, a colorimetric assay, an electrochemical assay, a lateral flow assay, or other dipstick assay. Preferably, the assay is a colorimetric assay where a change in colour of components in a solution can be measured.

In an embodiment of the first aspect, the assay comprises coating of a NP with the polynucleotide sequence.

In an embodiment of the first aspect, the coating of the NP with the polynucleotide sequence is reversible.

In an embodiment of the first aspect, there is an increase in the $\zeta$-potential value of the aptamer coated NP when compared to a bare NP.

In an embodiment of the first aspect, the aptamer may optionally include a fluorescent tag.

In an embodiment of the first aspect, the aptamer is specific for small target molecules and other target substrates such as proteins, antibodies, biological markers, ions and derivatives and/or metabolites of the aforementioned.

The small target molecules and/or other target substrates to be detected may be selected from chemicals that mimic hormones, hormones, naturally occurring phytoestrogens, narcotics and metabolites thereof. Preferably, the small molecule is an endocrine disrupting compound, a steroidal sex hormone, metabolites or synthetic variants thereof. More preferably, the small molecule is selected from endocrine disrupting compounds, and metabolites thereof. More preferably, the small molecule belongs to the estrogenic family of compounds. Even more preferably, the small molecules are selected from 17β-oestradiol (E2); oestrone; oestriol; androstenedione; testosterone; dihydrotestosterone; pregnenolone; progesterone; 17α-hydroxyprogesterone, 17α-ethynylestradiol; isoflavones; lignans; coumestans; organohalides including organochlorines, polychlorinated organic compounds, polychlorobiphenyl (PCB); alkylphenols; alkylphenol ethoxylates; phthalates; bisphenol-A (BPA); Bis (4-hydroxyphenyl) methane; cholesterol; adenosine; triclosan; or synthetic steroids such as diethylstilboestrol (DES); cocaine, heroin and any metabolites of the mentioned compounds thereof. Even more preferably, the small molecule to be detected is selected from 17β-oestradiol, testosterone, progesterone, and adenosine.

Alternatively, the small target molecules and/or other target substrates to be detected may also be hormone or a marker of a condition of disease in a body. For example, the aptamer could be selective for the detection of hormones and/or metabolites to establish fertility, or status in an animal. Alternatively, the aptamer can be selected for the detection of known markers of disease, for example overexpression of a cancer gene to detect cancer, detection of molecules associated with infection, or to establish levels of specific metabolites associated with a particular condition.

The target substrate to be detected may also include ions, such as ions selected from bromide, cadmium, calcium, cerium, chloride, copper, fluoride, iodide, iron, lanthanum, lead, nitrate, potassium, sodium, strontium, sulphate, and zinc, In an embodiment of the first aspect, the aptamer detects small target molecules and/or other target substrates present in a sample. The sample may be an environmental sample, for example a water sample, soil sample, or even a plant sample. Alternatively, the sample may be from an animal, for example a tissue sample, a hair or wool sample, a urine sample, a blood sample, a serum sample, a saliva sample or a faecal sample.

In an embodiment of the first aspect, the nanoparticle may be selected from nanoparticles, microparticles and quantum dots. Even more preferably the nanoparticle is derived from a noble metal. The noble metal may be selected from gold, ruthenium, rhodium, palladium, silver, and platinum. Preferably the nanoparticle is a gold nanoparticle.

In an embodiment of the first aspect the aptamer detects levels of the small target molecules and/or other target substrates in the sample in a range of from about 1 pM to about 100 µM. More preferably, the aptamer detects the small target molecules and/or other target substrates in the sample in the range of from about 1 pM to about 100 µM. Even more preferably, the aptamer detects the small target molecules and/or other target substrates in the range of from about 200 pM to about 400 nM.

In an embodiment of the first aspect, the binding of the aptamer to the small target molecules and/or other target substrates is indicated by a measureable change in the assay. The assay is preferably a colorimetric assay wherein the change is a colorimetric change. The colorimetric change may be identified by techniques such as UV-Vis spectroscopy. Preferably, the colorimetric change is visible to the naked eye.

In a second aspect, the invention provides for a colorimetric assay method for detecting a small target molecule and/or other target substrates in a sample, wherein the method comprises:
  i) contacting a polynucleotide surface coated particle with the sample, said polynucleotide comprising a nucleotide binding domain specific for the small target molecules and/or other target substrates, and additional bases; and
  ii) measuring any change in colour of the coated particle and sample combination wherein a colour change is indicative of the presence of the small target molecules and/or other target substrates;

wherein, the polynucleotide is optimised to comprise additional nucleotide bases.

In an embodiment of the second aspect, the polynucleotide is an aptamer. Preferably, the aptamer is selected from an ssDNA aptamer and an RNA aptamer. Most preferably, the aptamer is ssDNA.

In an embodiment of the second aspect, the additional nucleotide bases are situated at an end selected from the 5' end, the 3' end or the 5' and 3' ends.

In an embodiment of the second aspect, the method further comprises comparing two or more polynucleotide sequences, wherein at least one polynucleotide sequence has one or more additional nucleotide bases, and selecting a preferred polynucleotide sequence to use in the assay based on optimal sensitivity toward the small target molecule and/or other target substrates in the assay.

In another embodiment of the second aspect, the additional nucleotide bases comprise from 1 to 10 nucleotide bases at the selected end or ends. Preferably, the additional nucleotide bases comprise from 2 to 8 additional nucleotide bases at the selected end or ends. Most preferably, the additional nucleotide bases comprise from 4 to 7 nucleotide bases at the selected end or ends. The additional nucleotide bases may be selected from 1, 2, 3, 4, 5, 6, 7, 8, 9 and 10 nucleotide bases.

In another embodiment of the second aspect, the additional nucleotide bases comprise from 1 to 10 nucleotide bases at the selected end or ends. Preferably, the additional nucleotide bases comprise from 2 to 8 additional nucleotide bases at the selected end or ends. Most preferably, the additional nucleotide bases comprise from 4 to 7 nucleotide bases at the selected end or ends. The additional nucleotide bases may be selected from 1, 2, 3, 4, 5, 6, 7, 8, 9 and 10 nucleotide bases at the 3' end and/or 1, 2, 3, 4, 5, 6, 7, 8, 9 and 10 nucleotide bases at the 5' end.

In an embodiment of the second aspect, the additional nucleotide bases are sufficient to allow binding of the polynucleotide sequence (aptamer) to the nanoparticle and the target substrate.

In an embodiment of the second aspect, the additional nucleotide bases do not suppress signal transduction.

In an embodiment of the second aspect, the coating of the NP with the polynucleotide sequence is reversible.

In an embodiment of the second aspect, there is an increase in the ζ-potential value of the aptamer coated NP when compared to a bare NP.

In an embodiment of the second aspect, the aptamer may optionally include a fluorescent tag.

In an embodiment of the second aspect, the aptamer is specific for small target molecules and/or other target substrates such as small target molecules, proteins, antibodies, markers, ions and derivatives and metabolites of the aforementioned.

The small target molecules and/or other target substrates to be detected may be selected from chemicals that mimic hormones, hormones, naturally occurring phytoestrogens, narcotics and metabolites thereof. Preferably, the small molecule is an endocrine disrupting compound, a steroidal sex hormone, metabolites or synthetic variants thereof. More preferably, the small molecule is selected from endocrine disrupting compounds, and metabolites thereof. More preferably, the small molecule belongs to the estrogenic family of compounds. Even more preferably, the small molecules are selected from 17β-oestradiol (E2); oestrone; oestriol; androstenedione; testosterone; dihydrotestosterone; pregnenolone; progesterone; 17α-hydroxyprogesterone, 17α-ethynylestradiol; isoflavones; lignans; coumestans; organohalides including organochlorines, polychlorinated organic compounds, polychlorobiphenyl (PCB); alkylphenols; alkylphenol ethoxylates; phthalates; bisphenol-A (BPA); Bis (4-hydroxyphenyl) methane; cholesterol; adenosine; triclosan; or synthetic steroids such as diethylstilboestrol (DES); cocaine, heroin and any metabolites of the mentioned compounds thereof. Even more preferably, the small molecule to be detected is selected from 17β-oestradiol, testosterone, progesterone, and adenosine.

Alternatively, the small target molecules and/or other target substrates to be detected may also be hormone or a marker of a condition of disease in a body. For example, the aptamer could be selective for the detection of hormones and/or metabolites to establish fertility, or status in an animal. Alternatively, the aptamer can be selected for the detection of known markers of disease, for example overexpression of a cancer gene to detect cancer, detection of molecules associated with infection, or to establish levels of specific metabolites associated with a particular condition.

The small target molecules and/or other target substrates to be detected may also include ions, such as ions selected from bromide, cadmium, calcium, cerium, chloride, copper, fluoride, iodide, iron, lanthanum, lead, nitrate, potassium, sodium, strontium, sulphate, and zinc, In an embodiment of the second aspect, the aptamer detects small target molecules and/or other target substrates are present in a sample. The sample may be an environmental sample, for example a water sample, soil sample, or even a plant sample. Alternatively, the sample may be from an animal, for example a tissue sample, a hair or wool sample, a urine sample, a blood sample, a serum sample, a saliva sample or a faecal sample.

In an embodiment of the second aspect, the nanoparticle may be selected from nanoparticles, microparticles and quantum dots. Even more preferably the nanoparticle is derived from a noble metal. The noble metal may be selected from gold, ruthenium, rhodium, palladium, silver, and platinum. Preferably the nanoparticle is a gold nanoparticle.

In an embodiment of the second aspect the aptamer detects levels of the small target molecules and/or other target substrates in the sample in a range of from about 1 pM to about 100 μM. More preferably, the aptamer detects the small target molecules and/or other target substrates in the sample in the range of from about 1 pM to about 100 μM. Even more preferably, the aptamer detects the small target molecules and/or other target substrates in the range of from about 200 pM to about 400 nM.

In an embodiment of the second aspect, the binding of the aptamer to the small target molecules and/or other target substrates is indicated by a colorimetric change in the colorimetric assay. The colorimetric change may be identified by techniques such as UV-Vis spectroscopy. Preferably, the colorimetric change is visible to the naked eye.

In a third aspect, the invention provides a colorimetric assay for detecting a small target molecule and/or other target substrates in a sample, wherein the method comprises:
 i) contacting an polynucleotide with a particle to coat the surface of the particle to provide a coated particle;
 ii) contacting the polynucleotide coated particle with a sample;
 iii) incubating the sample;
 iv) analysing the sample and measuring change in colour wherein the colour change is indicative of the presence of the small target molecules and/or other target substrates; and
 wherein, the polynucleotide is optimised to comprise additional nucleotide bases and the polynucleotide sequence v) comprises a ligand binding domain,
 vi) binds the particle; and
 vii) the additional bases provide optimal signal transduction.

In an embodiment of the third aspect, the polynucleotide is an aptamer. Preferably, the aptamer is selected from an ssDNA aptamer and an RNA aptamer. Most preferably, the aptamer is ssDNA.

In an embodiment of the third aspect, the additional nucleotide bases are situated at an end selected from the 5' end, the 3' end or the 5' and 3' ends.

In an embodiment of the third aspect, the method further comprises comparing two or more polynucleotide sequences, wherein at least one polynucleotide sequence has one or more additional nucleotide bases, and selecting a preferred polynucleotide sequence to use in the assay based on optimal sensitivity toward the small target molecule and/or other target substrates in the assay.

In another embodiment of the third aspect, the additional nucleotide bases comprise from 1 to 10 nucleotide bases at the selected end or ends. Preferably, the additional nucleotide bases comprise from 2 to 8 additional nucleotide bases at the selected end or ends. Most preferably, the additional nucleotide bases comprise from 4 to 7 nucleotide bases at the selected end or ends. The additional nucleotide bases may be selected from 1, 2, 3, 4, 5, 6, 7, 8, 9 and 10 nucleotide bases.

In another embodiment of the third aspect, the additional nucleotide bases comprise from 1 to 10 nucleotide bases at the selected end or ends. Preferably, the additional nucleotide bases comprise from 2 to 8 additional nucleotide bases at the selected end or ends. Most preferably, the additional nucleotide bases comprise from 4 to 7 nucleotide bases at the selected end or ends. The additional nucleotide bases may be selected from 1, 2, 3, 4, 5, 6, 7, 8, 9 and 10 nucleotide bases at the 3' end and/or 1, 2, 3, 4, 5, 6, 7, 8, 9 and 10 nucleotide bases at the 5' end.

In an embodiment of the third aspect, the additional nucleotide bases are sufficient to allow binding of the polynucleotide sequence (aptamer) to the nanoparticle and the target substrate.

In an embodiment of the third aspect, the additional nucleotide bases do not suppress signal transduction.

In an embodiment of the third aspect, the coating of the NP with the polynucleotide sequence is reversible.

In an embodiment of the third aspect, there is an increase in the ζ-potential value of the aptamer coated NP when compared to a bare NP.

In an embodiment of the third aspect, the aptamer may optionally include a fluorescent tag.

In an embodiment of the third aspect, the aptamer is specific for small target molecules and/or other target substrates such as small target molecules, proteins, antibodies, markers, ions and derivatives and metabolites of the aforementioned.

The small target molecules and/or other target substrates to be detected may be selected from chemicals that mimic hormones, hormones, naturally occurring phytoestrogens, narcotics and metabolites thereof. Preferably, the small molecule is an endocrine disrupting compound, a steroidal sex hormone, metabolites or synthetic variants thereof. More preferably, the small molecule is selected from endocrine disrupting compounds, and metabolites thereof. More preferably, the small molecule belongs to the estrogenic family of compounds. Even more preferably, the small molecules are selected from 17β-oestradiol (E2); oestrone; oestriol; androstenedione; testosterone; dihydrotestosterone; pregnenolone; progesterone; 17α-hydroxyprogesterone, 17α- ethynylestradiol; isoflavones; lignans; coumestans; organohalides including organochlorines, polychlorinated organic compounds, polychlorobiphenyl (PCB); alkylphenols; alkylphenol ethoxylates; phthalates; bisphenol-A (BPA); Bis (4-hydroxyphenyl) methane; cholesterol; adenosine; triclosan; or synthetic steroids such as diethylstilboestrol (DES); cocaine, heroin and any metabolites of the mentioned compounds thereof. Even more preferably, the small molecule to be detected is selected from 17β-oestradiol, testosterone, progesterone, and adenosine.

Alternatively, the small target molecules and/or other target substrates to be detected may also be hormone or a marker of a condition of disease in a body. For example, the aptamer could be selective for the detection of hormones and/or metabolites to establish fertility, or status in an animal. Alternatively, the aptamer can be selected for the detection of known markers of disease, for example overexpression of a cancer gene to detect cancer, detection of molecules associated with infection, or to establish levels of specific metabolites associated with a particular condition.

The small target molecules and/or other target substrates to be detected may also include ions, such as ions selected from bromide, cadmium, calcium, cerium, chloride, copper, fluoride, iodide, iron, lanthanum, lead, nitrate, potassium, sodium, strontium, sulphate, and zinc, In an embodiment of the third aspect, the aptamer detects small target molecules and/or other target substrates are present in a sample. The sample may be an environmental sample, for example a water sample, soil sample, or even a plant sample. Alternatively, the sample may be from an animal, for example a tissue sample, a hair or wool sample, a urine sample, a blood sample, a serum sample, a saliva sample or a faecal sample.

In an embodiment of the third aspect, the nanoparticle may be selected from nanoparticles, microparticles and quantum dots. Even more preferably the nanoparticle is derived from a noble metal. The noble metal may be selected from gold, ruthenium, rhodium, palladium, silver, and platinum. Preferably the nanoparticle is a gold nanoparticle.

In an embodiment of the third aspect the aptamer detects levels of the small target molecules and/or other target substrates in the sample in a range of from about 1 pM to about 100 μM. More preferably, the aptamer detects the small target molecules and/or other target substrates in the sample in the range of from about 1 pM to about 100 μM. Even more preferably, the aptamer detects the small target molecules and/or other target substrates in the range of from about 200 pM to about 400 nM.

In an embodiment of the third aspect, the binding of the aptamer to the small target molecules and/or other target substrates is indicated by a colorimetric change in the colorimetric assay. The colorimetric change may be identified by techniques such as UV-Vis spectroscopy. Preferably, the colorimetric change is visible to the naked eye.

DETAILED DESCRIPTION

Definitions

Unless the context clearly requires otherwise, throughout the description and the claims, the words "comprise", "comprising" and the like, are to be construed in an inclusive sense as opposed to an exclusive or exhaustive sense, that is to say, in the sense of "including, but not limited to".

The term "animal" is intended to mean human and non-human subjects. For example, humans; domesticated stock including cows, sheep, goats, horses, pigs; domesticated pets including cats, dogs; wild animals including monkeys, birds, amphibians, reptiles; aquatic life forms such as fish.

The term "aptamer" as described herein is intended to mean a single strand of RNA or DNA that specifically binds to particular target molecules and/or other target substrates. The term "aptamer" relates to polynucleotide or oligonucleotide sequences. The terms "polynucleotide" or "oligonucleotide" may be used interchangeably and is a term commonly used and understood within the art. Those skilled in the art will readily understand that variation in the sequence code of the aptamer may be varied by standard methodology without substantially affecting the binding of the substrate to the NP-aptamer conjugate.

The term "colorimetric assay" is an analytical technique that measures the concentration of coloured components of a solution.

The term "conformational changes" means a change in the conformational form of the aptamer, for example, a change from a tightly folded structure to a loose linear-type structure that results in opening up of the binding site, or from a loose linear-type structure to a tightly folded structure. This type of alteration would be readily understood by those skilled in the art.

The term "estrogenic family" of compounds means compounds that are chemically related to estrogens. Estrogenic compounds may be natural or synthetic, steroidal or non-steroidal, and includes metabolites of such compounds.

The term "flanking sequences" means non-binding portion of a nucleotide sequences that can bind to a target substrate and may include primers that are used in the preparation of the nucleotide sequence.

The term "increasing the ζ-potential value" means that the value becomes more negative. This would be readily understood and appreciated by those of skill in the art.

The term "moderate salt concentration(s)" means ionic strength of up to about 30 mM.

The term "NP" or "nanoparticle" is also intended to encompass microparticles and quantum dots as well as nanoparticles. That is, nanoparticles, microparticles or quantum dots may be used, and use of one term throughout the specification is not intended to exclude the others, unless expressly stated. The term "NP" or "nanoparticle" is used throughout for convenience and consistency.

The term "relatively high concentration of aptamers" means greater than about 100 nM.

The term "relatively high E2 concentrations" means concentrations of about 1 μM.

The term "sample" is intended to mean a sample isolated or collected from an environmental or biological source and is located ex vivo. The sample may be of biological origin, isolated from an animal or may be collected from the environment. Sources of samples may include without limitation, for example soils, waterways, tissue, blood, serum, urine, saliva, faeces, hair and wool.

The term "salt" is intended to apply to non-toxic salts derived from inorganic or organic acids, including, but not limited by the following salts: halides (chloride, bromide, iodide fluoride), acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, hydrochloride, hydrobromide, hydroiodide, 2-hydroxyethanesulfonate, lactate, maleate, malonate, methanesulfonate, nitrate, oxalate, persulfate, phosphate, picrate, pivalate, propionate, p-toluenesulfonate, salicylate, succinate, sulfate, tartrate, thiocyanate, and undecanoate, and may comprise the cations selected from $Na^+$, $K^+$, $Ca^{2+}$, $Mg^{2+}$, $Li^+$.

The term "signal transduction" means generating an observable response from aptamer-target recognition in a given assay system. For example, in a colorimetric assay, the signal transduction refers to the observable change from the aptamer binding to the target.

The term "optimal signal transduction" means the conditions and/or aptamer that gives the best signal transduction for a given assay.

The term "small molecule" is intended to mean compounds of simple molecular structure with a Mw of from about 60 to about 2000 g $mol^{-1}$, preferably in the range of from about Mw 100 to 500 g $mol^{-1}$, more preferably of from about 150 to 350 g $mol^{-1}$. The molecular weight of such compounds and the calculation of the molecular weights are well known to those of skill in the art. Such compounds include, without limitation, hormone mimics, hormones, naturally occurring phytoestrogens, narcotics and metabolites thereof, organohalides and compounds such as 17β-oestradiol (E2); oestrone; oestriol; androstenedione; testosterone; dihydrotestosterone; pregnenolone; progesterone; 17α-hydroxyprogesterone, 17α-ethynylestradiol; isoflavones; lignans; coumestans; organohalides including organochlorines, polychlorinated organic compounds, polychlorobiphenyl (PCB); alkylphenols; alkylphenol ethoxylates; phthalates; bisphenol-A (BPA); Bis (4-hydroxyphenyl) methane; cholesterol; adenosine; triclosan; or synthetic steroids such as diethylstilboestrol (DES); cocaine, heroin and any metabolites of the mentioned compounds thereof.

The term "other target substrate" is intended to mean substrates that selectively bind to an aptamer. Target substrates, include without limitation, active pharmaceutical drugs, antibodies, biomarkers that may be indicative of a disease or condition, proteins, ions, recreational drugs, small molecules, and/or metabolites of the aforementioned.

As used in the specification and the appended claims, the singular forms "a," "an" and "the" include plural referents unless the context clearly dictates otherwise.

Discussion

It is generally acknowledged that the closer identity that a polynucleotide sequence (aptamer) has to the ligand binding domain of a target substrate, the higher the affinity and the better the interaction between the polynucleotide sequence and the target substrate. That is, by having less non-binding sequences present, which may interfere with target substrate binding, then the sequence will have a high binding affinity.

The present inventors have surprisingly shown that nucleotide bases in addition (i.e. excess) to the ligand binding domain are an important element for effective binding interactions in a nanoparticle assay.

Furthermore, a small number of nucleotide bases additional to the ligand binding domain are required for optimal activity of the invention in an assay, particularly a calorimetric nanoparticle assay.

Without wishing to be bound by theory, it is thought that truncated aptamer consisting essentially of the ligand binding domain does not have sufficient enough nucleotide bases to interact with the particles (nanoparticles, microparticles and quantum dots) together with small target molecules and/or other target substrates. That is, when the short LBD only sequence binds to a nanoparticle, this reduces the ability of the LBD to access the target substrate. Therefore, the ligand binding domain requires extra nucleotides at the 5' end, the 3' end or both the 3' and 5' end. These extra bases facilitate biding to both the particle and the target substrate without compromising or suppressing the signal transduction This has been shown by providing a family of aptamers of different lengths, for example: a long length aptamer (e.g. 75-mer), a mid-length (e.g. 35-mer aptamer), and a short-length aptamer (e.g. 22-mer). The present invention therefore includes producing variants with 1 or more nucleotide bases in excess of the LBD and using these variants in an assay.

The specific 35-mer sequence: AAGGGATGC-CGTTTGGGCCCAAGTTCGGCATAGTG SEQ ID No: 2, has a surprising and marked increase in its affinity to estrogenic type compounds. Specifically the 35-mer aptamer (SEQ ID No: 2) is particularly effective in colorimetric aggregation assays as a means for the detection of small molecules in samples, allowing detection in the pM range compared to the detection in the nM range for the 75-mer E2 aptamer of sequence 5'-ATACGAGCTTGTTCAATAC-GAAGGGATGCCGTTTGGGCCCAAGTTCGGCATAGT-GTGG TGATAGTAAGAGCAATC-3' (SEQ ID No: 1).

The provision of a 22-mer aptamer consisting essentiality of the ligand binding domain, was shown to provide decreased activity with respect the 35-mer (SEQ ID No: 2) and the 75-mer aptamers (SEQ ID No: 1), indicating that some additional nucleotide sequences outside of the ligand binding domain are required for effectiveness in the colorimetric assay method disclosed herein.

Optimisation Method:

Once it has been appreciated by one skilled that art that the additional residues can be beneficial to the sensitivity of the colorimetric assay, then the inventors have devised a method for finding the optimal sequence for use in an aptamer based assay. Specifically, the presence of additional residues allows for the optimisation of the colorimetric assay. Essentially the method provides for the production of a multiple number of polynucleotide sequences that contain one or more additional nucleotides bases at one or both ends, in addition of the LBD. Ideally the range of polynucleotides contain between one and ten addition residues, in addition to the LBD, at both ends of the LBP sequence.

The range of polynucleotides tested and one or more selected to provide optimal signal transduction while maintaining sufficient binding interaction of the polynucleotide sequence (aptamer) with the nanoparticle, microparticle or quantum dot together with a sufficient binding interaction with the small target molecules and/or other target substrates. That is, that despite having additional nucleotide bases on the polynucleotide sequence, the signal transduction is not substantially suppressed and the binding interactions are also not negatively affected. This is achieved by testing each of the polynucleotides in the assay system to see which one provides for the best sensitivity and accuracy. The nucleotide sequence having the optimal sensitivity towards the small target molecules and/or other target substrates is then selected for use in the assay.

It is important to note, that the method allows a given aptamer to be optimised to give an optimal signal transduction for a given assay system, rather than simply cutting an aptamer as close as possible to the LBD, or selecting a sequence purely on relative Kd values to the target molecule. Rather, the method is based on the surprising finding that having additional residues can be important, and that a sequence should be tailored to give the optimal signal transduction for a given assay system.

Aptamer Production:

SELEX, or System Evolution of Ligands by Exponential Enrichment is a known method for producing single stranded DNA or RNA molecules that specially bind to a target (Ellington A D & Szostak J W (1990). Nature. 346:818-822, 2 and Blackwell T K & Weintraub H (1990) Science 250:1104-1110). Briefly the process involves the production a library of random sequences of a fixed length. The library includes fixed sequences at each end, which act as primers. The library is then exposed to the target of interest and the sequences that bind selected for. The selected primers are then amplified (using the primers sequences) and then subjected to various rounds of increasing stringent conditions, eventually leading to the selection of sequences the can bind to the target molecules with high affinity. The compounds can also be selected based on specificity and not just by binding of the target.

A range of polynucleotides having a number of extra bases in addition to the LBD can be produced using methods known in the art. Such methods can include using methods (for example use of restriction enzymes, or any enzyme that cuts polynucleotide sequences) to cleave a longer sequence (produced, from, for example, the SELEX process), at various points radiating away from the LBP sequence. In using different cutting points, a range of polynucleotides, having a range of lengths radiating out from the LBD can be produced for testing.

Alternatively, the longer peptide produced can be cut to the LBD, and then extended in either, or both directions using methods such as primer extension PCR, or direct chemical addition, to provide a range of additional bases to the LBD for testing.

Another method is provided where the sequence of the binding domain is known. When the LBD is known, a range of polynucleotides can be directly chemically synthesised to include a range of additional bases to the LBD for testing.

If certain bases are known to be beneficial to aid in binding the polynucleotide to the nano particle, then such residues can be used in the additional bases. Alternatively, random bases can be included, and then by including not only a random set of lengths, but also lengths containing random additional bases. In doing so, the polynucleotide can be further optimised for the given assay system based on the type of bases as well as the number of bases.

Colorimetric Assay

In accordance with the present invention, the optimisation of polynucleotide sequences may be used in a colorimetric assay. The polynucleotide sequences (aptamers) are mixed with nanoparticles, and the aptamer coats the nanoparticles. It will be appreciated by those of skill in the art that the term "nanoparticle" is intended to include nanoparticles (NP), microparticles and quantum dots. That is, nanoparticles, microparticles or quantum dots may be used, and use of one term is not intended to limit and/or exclude the other types of particles, unless expressly stated.

The electrostatic repulsion between the negatively charged phosphate backbone of aptamer and the citrate surface of the nanoparticles is balanced by the attractive interaction of nitrogen bases, with the NP surfaces [Brown, K. A., et al, 2008, *J. Phys. Chem. C*, 112, 7517-7521]. This also results in an increase in the $\zeta$-potential value of the NPs, for example from −23.5 mV (±0.28) to −40.2 mV (±0.9) and confirms adsorption of the aptamer to the nanoparticles, leading to a dispersion of aptamer coated NPs in solution that are also stable in moderate salt concentrations up to approximately 30 mM ionic strength. When the aptamer binds to a target molecule and/or other target substrates, a conformational change in the aptamer is induced and this reduces the aptamer's affinity to the NPs. The NP-aptamer dispersion thereby becomes destabilised towards salt [McKeague, et al, 2012, *J. Nucleic Acids*, 748913 and Stoltenburg, R., et al., 2007, *Biomol. Eng.*, 24, 381-403] and the target-bound aptamers dissociate from the NP surface (FIG. 1B). At an optimum ionic strength, the presence of the target small molecule and/or other target substrate is identified by a colour change observed when the free NPs (those that are no longer protected by aptamers), aggregate with the target small molecule and/or other target substrate (FIG. 1A).

The degree of aggregation of the NPs to the target small molecule and/or other target substrate can be quantified by UV-vis absorption and is evident to the naked eye. The aggregation of the NPs to the target small molecule and/or other target substrate is indicated by the colour observed. However, the colour change is dependent on the concentration of the target small molecule and/or other target substrate in the sample [Kim, Y. S., et al., 2010, *Biosens. Bioelectron.*, 26, 1644-9; Li, H., Rothberg, L., 2004, *Proc. Natl. Acad. Sci. U.S.A.*, 101, 14036-9; Mei, Z., et al., 2013, *Biosens. Bioelectron.*, 39, 26-30; Shi, H., et al., 2013, *J. Hazard. Mater.*, 260, 754-761; Song, K.-M., et al., 2011, *Anal. Biochem.*, 415, 175-81; Yang, C., et al., 2011, *Biosens. Bioelectron.*, 26, 2724-7; Zheng, Y., 2011, *Sensors Actuators B Chem.*, 156, 95-99].

The NPs selected for use with the aptamer in the invention must exhibit a change in optical absorption when aggregation is induced. In the case of noble metal nanoparticles such as gold, the surface plasmon resonance is very sensitive to aggregation, resulting in a strong visible signature. Other types of nanoparticles or microparticles could alternatively be used, including semiconducting particles, quantum dots or polymer nanoparticles.

The method of the present invention may be especially useful in human, or veterinary medicine. Such a method can be provided by colorimetric assays which can provide quick visual indication of the presence of target substrates compared to standard analytical methodologies such as chromatography and mass spectrometry.

75-mer E2 Aptamer (SEQ ID No: 1)

When the 75-mer E2 aptamer (SEQ ID No: 1) is mixed with AuNPs, the $\zeta$-potential value of the AuNPs increases from −23.5 mV (±0.28) to −40.2 mV (±0.9), and is confirmed via a titration with salt, as shown in FIG. 2. Aggregation is evidenced by the reduced relative absorption of the unaggregated (free) AuNP surface plasmon peak at 523 nm compared to the aggregated NPs. The aptamer-coated AuNPs lose resistance towards salt after incubating with 100 nM E2, and the aptamer dissociates from the AuNP surface (completely or partially) when binding to E2.

This is supported by the less negative $\zeta$-potential (−32.3 mV (±0.9)) measured for the AuNP-75-mer after incubation with 1000 nM E2. FIG. 2 also identifies the optimal salt concentration required (23.8 mM) for E2 detection for the 75-mer aptamer. The AuNP-75-mer dispersion is on the edge of its stability and the introduction of E2 triggers significant aggregation.

It can be seen in FIG. 3 that the AuNP-75-mer aptamer system results in detection of E2 at concentrations above 5 nM when aggregation is measured via absorption spectroscopy. 100 nM E2 can be easily visualised by the naked-eye. Binding induced aggregation turns the pink/red colloidal solution to purple/blue (FIG. 4). Transmission electron microscopy and dynamic light scattering measurements exhibit larger aggregates in the presence of E2 consistent with E2-induced aggregation with the AuNPs (FIG. 13-FIG. 16). The lowest detected concentration of E2 using the 75-mer aptamer is 5 nM, with linearity ($R^2$=0.92) over the range from 5 nM to 400 nM, before saturation occurs. The colorimetric signals are confirmed as arising from a specific interaction with the aptamer. It is important to note that in a control experiment no colorimetric response is observed when E2 is incubated with bare AuNPs or with poly-T coated AuNPs. Poly-T presents similar electrostatic adsorption properties as the aptamer, and does not interact with targets through a 3D conformation.

Progesterone (P4) and testosterone (T) at 200 nM concentrations also exhibit a strong response when contacted with the AuNP-75-mer colloidal solutions. Testosterone triggers a 55% response and progesterone a 68% response relative to E2 (FIG. 5). However, the 75-mer E2 aptamer does not show any selectivity towards non-steroidal molecules (BPA and BPF).

35-mer E2 Aptamer (SEQ ID No:2)

The 75-mer aptamer (SEQ ID No: 1) is reduced to a 35-mer aptamer (SEQ ID No: 2) by the removal of the 20-mer flanking sequences to provide an aptamer of sequence AAGGGATGCCGTTTGGGCCCAAGTTCG-GCATAGTG (SEQ ID No: 2 and FIG. 6). In the CD spectrum (FIG. 7 and FIG. 8), it can be seen that on reducing the sequence from a 75-mer aptamer to a 35-mer aptamer, the minimum at 248 nm is retained; however, the 270 nm band splits into two overlapping bands at 265 nm and 295 nm, which collectively appear as a single broad feature. This change is a signature pattern of G-quadruplex formation [Karsisiotis, A. I., et al., 2011, *Angew. Chem. Int. Ed. Engl.*, 50, 10645-8; McManus, S. a, Li, Y., 2013, PLoS One, 8, e64131], and is consistent with previous reports showing that flanking sequences can hinder the formation of G-quadruplex structures [McManus, S. a, Li, Y., 2013, PLoS One, 8, e64131; Nonaka, Y., Sode, K., Ikebukuro, K., 2010, *Molecules*, 15, 215-25]. Incubation of the 35-mer aptamer with 10 μM E2 again show further changes in the CD spectrum. It should be noted that, the relatively high concentration of aptamers (greater than 100 nM) required to measure CD spectra can only be used to detect relatively high E2 concentrations (about 1 μM).

Adsorption of the 35-mer aptamer (SEQ ID No: 2) to the AuNPs is also confirmed by a more negative ζ-potential compared to the free AuNPs (from −23.5 mV (±0.28) to −29 mV (±1)). The smaller difference, compared to the 75-mer aptamer (vida supra), implies that there is a lesser degree of aptamer coverage on the AuNP. When the AuNP-35-mer aptamer (SEQ ID No: 2) is incubated with 1000 nM E2, the ζ-potential decreases to −25 mV (±0.2). This value is close to the original value of the bare AuNP, meaning that most of the aptamers have completely dissociated from the AuNP surface in the presence of 1000 nM E2.

The AuNP-35-mer aptamer has greater resistance to salt compared to the bare NPs (FIG. 9). Sensitivity toward E2 is confirmed by the partial loss of resistance observed after incubation with 100 nM E2. When the AuNP-35-mer aptamer (SEQ ID No: 2) is titrated with different concentrations of E2, detection levels of 200 pM are observed (FIG. 10). This result in 25-fold enhancement in the sensitivity of the AuNP-35-mer aptamer is observed under optimized salt concentration (23.8 mM), when compared with the 75-mer system (FIG. 4). This is a significant and unexpected degree of increase in sensitivity compared to the large 75-mer.

22-mer E2 Aptamer (SEQ ID No: 3)

The 75-mer aptamer is shortened to provide a 22-mer aptamer to reflect the proposed ligand binding domain for E2, (FIG. 11A).

The 22-mer aptamer (GCCGTTTGGGCCCAAGT-TCGGC) (SEQ ID No: 3) did not produce further improvement in aptamer dissociation from AuNPs compared to the 75-mer (SEQ ID No: 1) or the 35-mer aptamer (SEQ ID No: 2), even in spite of the more aggressive elimination of bases outside of the proposed target binding domain.

This observation is in line with smaller amplitude colorimetric sensing response compared with the 35-mer (SEQ ID No: 2) identified in FIG. 11B. It appears that retaining a small number of bases outside of the proposed binding region is optimal. This unexpected result highlights the fine balance that must be achieved between the aptamer's interaction with the AuNPs and with the target.

The 22-mer aptamer (SEQ ID No: 3) contains no redundancy outside of the proposed target-binding region; therefore, bases that are committed to target binding are unable to easily and simultaneously bind to AuNPs. Consequently, when the 22-mer aptamer (SEQ ID No: 3) is adsorbed to the AuNPs, the 22-mer aptamer (SEQ ID No:3) is proposed to be trapped in a structural arrangement that does not facilitate interaction with both the particle and the target. Target binding aptamer structures accessible in solution are note expected contribute to the assay if they are not first adsorbed to AuNPs. Conversely, the 35-mer (SEQ ID No: 2) has sufficient additional bases to simultaneously assist the adsorption of structures to the particle, present a favourable target binding domain (FIG. 18).

The present invention was also applied to the testing of E2 in rat urine using the E2 aptamers. Significant aggregation is observed when citrate coated AuNPs are exposed to 5% urine without additional salt (FIG. 17). The ionic strength of the rat urine (2.1 mM, as estimated by the conductivity measurement shown in FIG. 19) is too low to account for the aggregation based on the stability of AuNPs at up to 10 mM ionic strength in water. However, inclusion of the 35-mer aptamer (SEQ ID No: 2) prevents aggregation in the presence of 5% urine, and leads to tolerance towards ionic strengths of over 60 mM (over two-fold greater than in water). This observation highlights the potential of the urine matrix to interfere with aggregation based sensing, for example the ability of urine-based proteins and other molecules to sequester ions or adsorb on the surface of AuNPs. Repeating the salt titration experiment in the presence of E2 reveals an optimal ionic strength of 57 nM for sensing E2 in rat urine can be seen in FIG. 17a. FIG. 17b shows that E2 is detected visually and spectroscopically in concentration ranges from 5 nM up to 1 μM, with a linear response between 50 nM to 800 nM ($R^2$=0.95) before saturation occurs. FIG. 16c also confirms that the sensor retains excellent discrimination against potentially interfering molecules in urine, including those from the same steroidal hormone family. While the sensitivity is 25-fold lower than in water (FIG. 2, FIG. 10 and FIG. 12), the improvements resulting from removing a flanking nucleotide sequences are still enough to detect low concentrations of E2 in physiological fluids. On the other hand, the level of detection was found to increase by three orders of magnitude to 5 μM for the longer 75-mer system (SEQ ID No: 1) (FIG. 17b). It is ensured that specific binding interactions are resolved via the lack of response when the aptamers were replaced with poly-T.

The 75-mer, 35-mer and 22-mer aptamers (SEQ ID No: 1, SEQ ID No: 2 and SEQ ID No 3 respectively) comprising the ligand binding domain were also compared with non-specific (random) aptamer sequences (SEQ ID Nos: 4, 5, and 6; and Table 1). The non-specific (random) aptamer sequences (SEQ ID Nos: 4, 5, and 6) comprised of the nucleotide bases being arranged in a random order to eliminate the specific ligand binding domain, while containing the same total base composition. This was to establish that the colorimetric signals arose from a specific binding interaction with the aptamer comprising the ligand binding domain, rather than the colorimetric signal being caused by adsorption of E2 on the nanoparticle surface. No colorimetric response was observed when E2 was incubated with bare nanoparticles at the concentration ranges of interest.

Nanoparticles coated with the random 75-mer aptamer did not respond at all to E2. Increased ζ-potential and salt resistance compared with bare AuNPs confirmed that the random sequence still coats the AuNPs; however, the aptamers were unresponsive on incubation with E2 (FIG. 18).

domain (bases 18-52, indicated as the 'possible 35-mer'), as well as an additional 3-4 bases on each side to ensure that the new aptamer retains sufficient affinity to AuNPs. The optimal ionic strength for sensing with the 42-mer (SEQ ID No:8) was found to be 14.5 mM. The lower tolerance towards salt than the AuNP-75-mer (SEQ ID No: 7) indicates weaker affinity between the 42-mer aptamer (SEQ ID No:8) and AuNPs compared to the AuNP-75-mer system as a result of eliminating 33 nucleotides. However, the retained tolerance to salt confirms that the 42-mer (SEQ ID No: 8) has enough affinity to AuNPs to pursue sensing.

The 42-mer BRA aptamer (SEQ ID No:8) demonstrated an improved sensitivity towards BPA, and improved level of detection compared with the parent 75-mer (SEQ ID No:7).

TABLE 1

Aptamer Sequences

| | |
|---|---|
| E2 75-mer aptamer SEQ ID No: 1 | ATACGAGCTTGTTCAATACGAAGGGATGCCGTTTGGGCCCAA GTTCGGCATAGTGTGGTGATAGTAAGAGCAATC |
| E2 75-mer (random) SEQ ID No: 4 | AGGCCTAAGGGCATAATTAGCTCGAGCTCGAAAGGGGTTATA TGATGATTTGAATTCATGGGGCCCGACTCGGAT |
| E2 35-mer Aptamer SEQ ID No: 2 | AAGGGATGCCGTTTGGGCCCAAGTTCGGCATAGTG |
| E2 35-mer (random) SEQ ID No: 5 | ACGGGTGGCCGCCAGGTCTTGAAGTGGCAGTATTA |
| E2 22-mer Aptamer SEQ ID No: 3 | GCCGTTTGGGCCCAAGTTCGGC |
| E2 22-mer (random) SEQ ID No: 6 | TGGGCCCTTTACGGACCGCGTG |
| BPA 76-mer SEQ ID No: 7 | ATACGAGCTTGTTCAATAGGAAATCACGATTAGGTCCTCCGTC TGTGTGCGGTTGTGGTGATAGTAAGAGCAATC |
| BPA 42-mer SEQ ID No: 8 | CAATAGGAAATCACGATTAGGTCCTCCGTCTGTGTGCGGTTG |

75-mer BPA Aptamer (SEQ ID No: 7)

The 75-mer BPA aptamer (SEQ ID No: 7) and as shown in FIG. 24 was developed by the SELEX process to bind to the target BPA. Similar to the 75-mer E2 aptamer (SEQ ID No: 1), the 75-mer BPA aptamer (SEQ ID No: 7) was found to coat Au nanoparticles and enhance the stability of the dispersion to moderate salt concentrations. At the ionic strength of 23.8 nM, the aptamer coated AuNPs remain dispersed, yet removal of aptamers results in aggregation and a concomitant colour change. The colorimetric response towards the target BPA was therefore measured under these conditions, as shown in FIG. 23. The sensor response is indicated by an increasing ratio of the aggregate absorption at 625 nm to the dispersed AuNP absorption at 523 nm. The sensor responds approximately linearly up to 1 micromolar BPA. The level of detection is approximately 50 nM, based the error of two experiments. The response is shown to be specific to the 75-mer sequence used by comparing with a randomized 75-mer sequence of the same nucleotide composition. The random 75-mer exhibits a baseline response to BPA over the same concentration range.

42-mer BPA Aptamer (SEQ ID No: 8)

The 42-mer BPA aptamer (SEQ ID No: 8) (CAATAG-GAAATCACGATTAGGTCCTCCGTCTGTGTGCG-GTTG) and as shown in FIG. 24 was derived from the parent 75-mer BPA aptamer (SEQ ID No: 7). The 42-mer (SEQ ID No: 8) was selected based on retaining the central pair of stem-loop regions thought to contain the ligand binding The improved sensitivity is shown by the stronger colorimetric response towards BRA up to 1 micromolar. The level of detection is between 1 and 10 nM, as seen in the plot in FIG. 23B] The improved response of the 42-mer aptamer (SEQ ID No:8) over the 75-mer aptamer (SEQ ID No:7) is attributed to a better balanced affinity between the aptamer and the AuNPs, whereby the target bound aptamer readily dissociates from the AuNPs.

The inventors have successfully shown that the performance of the truncated aptamers comprises some nucleotides in excess of the LBD surpasses existing colorimetric aptasensors providing detection limits to pM levels. Without wishing to be bound by theory, it is thought that the improvement in sensitivity and selectivity can be attributed to two factors: i) improved aptamer affinity for small molecules and/or other target substrate, possibly associated with the observed stabilisation of G-quadraplexes when flanking sequences are eliminated, and ii) suppressed residual affinity of target bound aptamers to AuNPs.

The examples described herein are for purposes of illustrating embodiments of the invention. Other embodiments, methods, and types of analyses are within the capabilities of persons of ordinary skill in the art and need not be described in detail herein. Other embodiments within the scope are considered to be part of this invention.

Abbreviations

AuNP Gold nanoparticles
BPA bisphenol A

BPF Bis(4-hydroxyphenyl methane)
HAuCl$_4$ Chloroauric acid
DLS Dynamic Light Scattering
D$_f$ particle diffusion coefficient
E2 17β-oestradiol
FWHM Full Width at Half Maximum
MP microparticle
NP nanoparticle
PALS Phase Analysis Light Scattering
PTA Particle Tracking Analysis
P4 Progesterone
ssDNA single strand DNA
T Testosterone
RPS Resistive Pulse Sensing

EXAMPLES

17β-estradiol (E2), progesterone, testosterone, Bis(4-hydroxyphenyl methane) (BPF), bisphenol-A (BRA), E2 75-mer aptamer, truncated version 35-mer, poly-thymine (18) (poly T) Chloroauricacid (HAuCl$_4$) and sodium chloride (NaCl) are purchased from Sigma-Aldrich. The aptamers are dissolved in Milli-Q water and stored at −5° C. prior to use. Milli-Q water is used in all experiments (unless stated), and all other chemicals are of analytical grades purchased from standard chemical suppliers.

The aptamers of the present invention can be synthesised by standard synthetic methodologies commonly known and understood by those in the art for example, synthesis by SELEX.

General Procedure for the Synthesis of NPs:

Nanoparticles suitable for application with this invention can be prepared according to standard literature methods. For example: synthesis of AuNPs is described in Jana et al., 2001; synthesis of PtNPs is described in Teranishi at al., 1999; synthesis of AgNPs, is described by Yin at al., 2002; synthesis of PdNPs is described by Ge et al., 2007; synthesis of CoNPs is described by Redel et al., 2009; and synthesis of CuNPs can be found in Wu and Chen, 2004.

Figure 13:
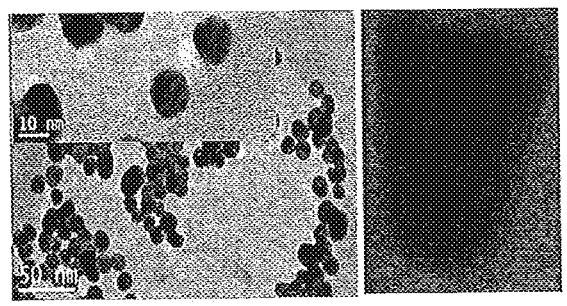
FIG. 13 TEM image (left) and photographs (right) showing the pinkish colour of AuNPs+0.1 nmol 75-mer aptamer FIG. 14 TEM image (left) and photographs (right) showing the pinkish-red colour of AuNPs+0.1 nmol 75-mer aptamer and the detection of 100 nM E2.
Figure 14:
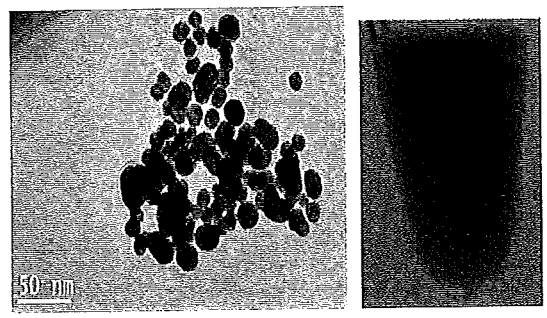
Figure 15:
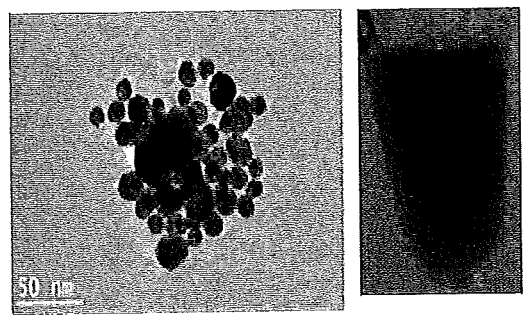
FIG. 15 TEM image (left) and photographs (right) showing the purplish-blue colour of AuNPs+0.1 nmol 75-mer aptamer and the detection of 400 nM E2.
Figure 16:
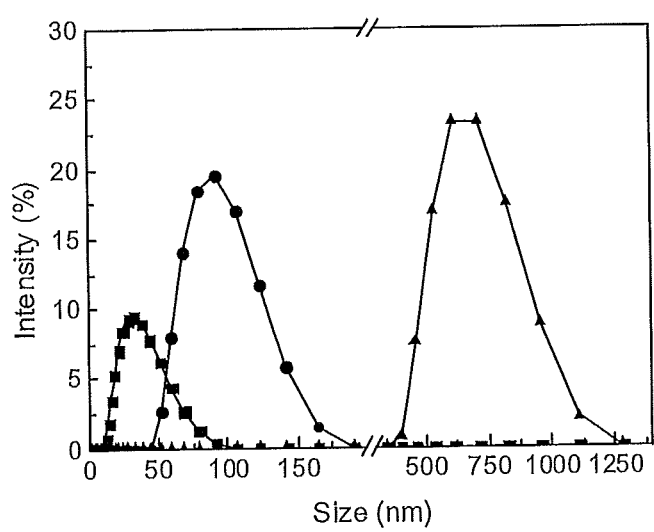
FIG. 16 shows DLS size characterisation for AuNPs+0.1 nmol 75-mer aptamer (■) and the detection of 100 nM E2 (●) and 400 nM (▲).
Figure 17:
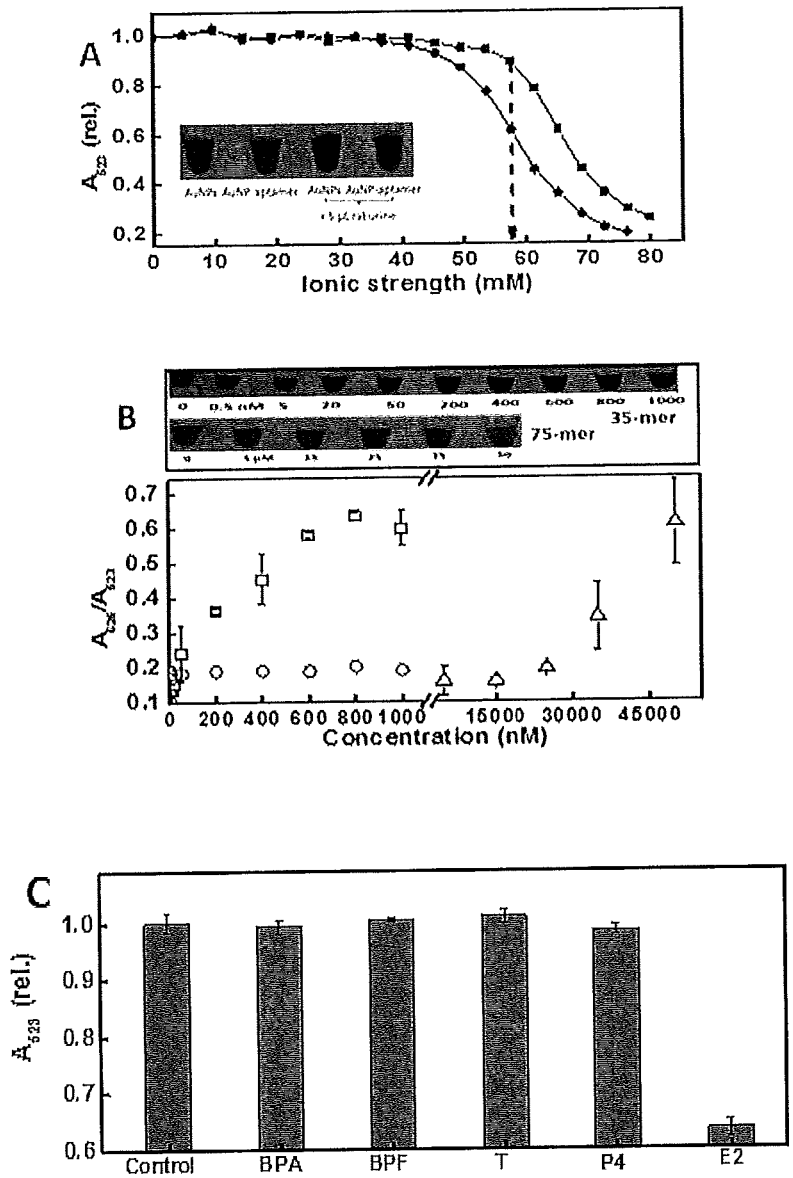
FIG. 17 (A) Salt dependent aggregation of AuNP-35-mer aptamer and AuNP-35-mer aptamer+100 nM E2 in rat urine (optimal salt concentration indicated by the black arrow). Photographs of AuNPs and AuNP-35-mer aptamer before and after addition of 5 μL rat urine are shown in the inset, legend: ●=35-mer+100 nM E2, ■=35-mer;
  (B) calorimetric aptasensor response towards a range of E2 concentrations in spiked rat urine using the AuNP-35-mer and AuNP-75-mer aptamers (photograph of the same samples in the top panel) compared with AuNP-poly-T control, legend: □-35-mer, ○-polyT, Δ-75-mer.
  (C) Specificity examinations of interfering molecules (at 200 nM) in rat urine samples using the AuNP-35-mer aptamer colloidal solution. Error bars indicate standard deviation of the mean of three experiments.
Figure 18:
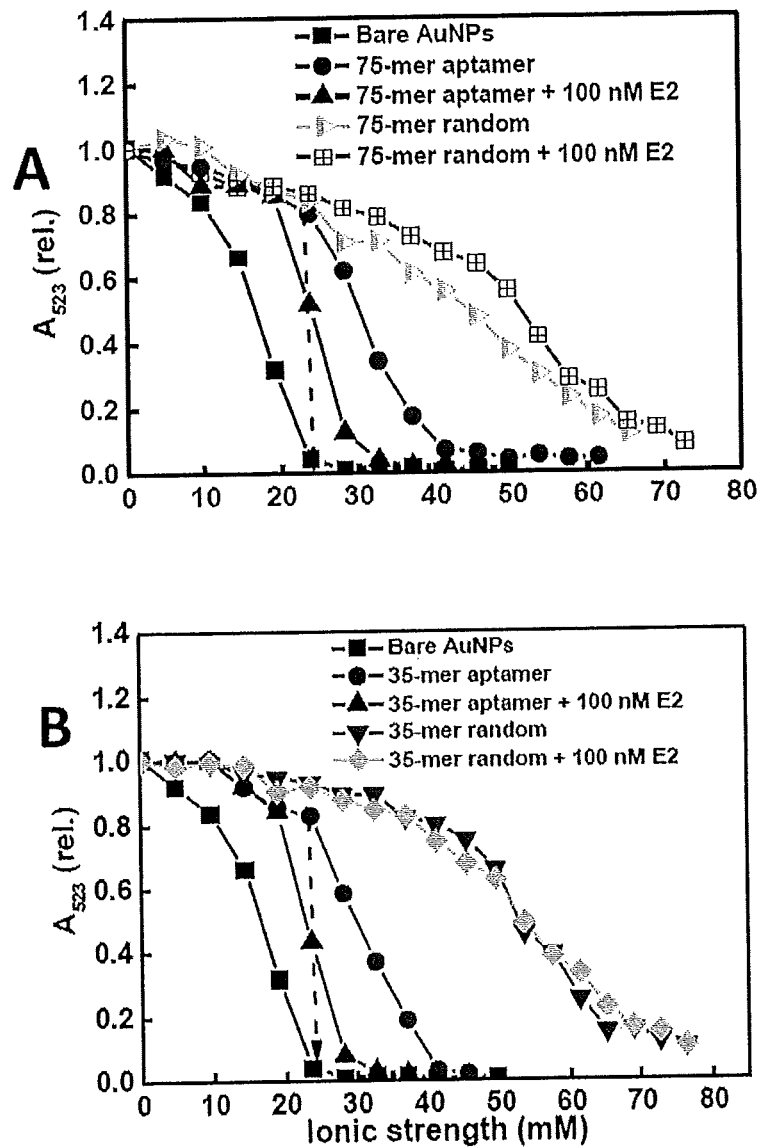
FIG. 18 (A) Salt dependent aggregation of AuNP-75-mer/AuNP-75-mer random DNA and AuNP-75-mer aptamer/AuNP-75-mer random DNA+100 nM E2 (optimal salt concentration indicated by the black arrow);
  (B) Salt dependent aggregation of AuNP-35-mer/AuNP-35-mer random DNA and AuNP-35-mer aptamer/AuNP-35-mer random DNA+100 nM E2 (optimal salt concentration indicated by the black arrow);
  (C) Salt dependent aggregation of AuNP-22-mer/AuNP-22-mer random DNA and AuNP-22-mer aptamer/AuNP-22-mer random DNA+100 nM E2 (optimal salt concentration indicated by the black arrow);
  (D) Same as (B) but in urine samples.
Figure 18:
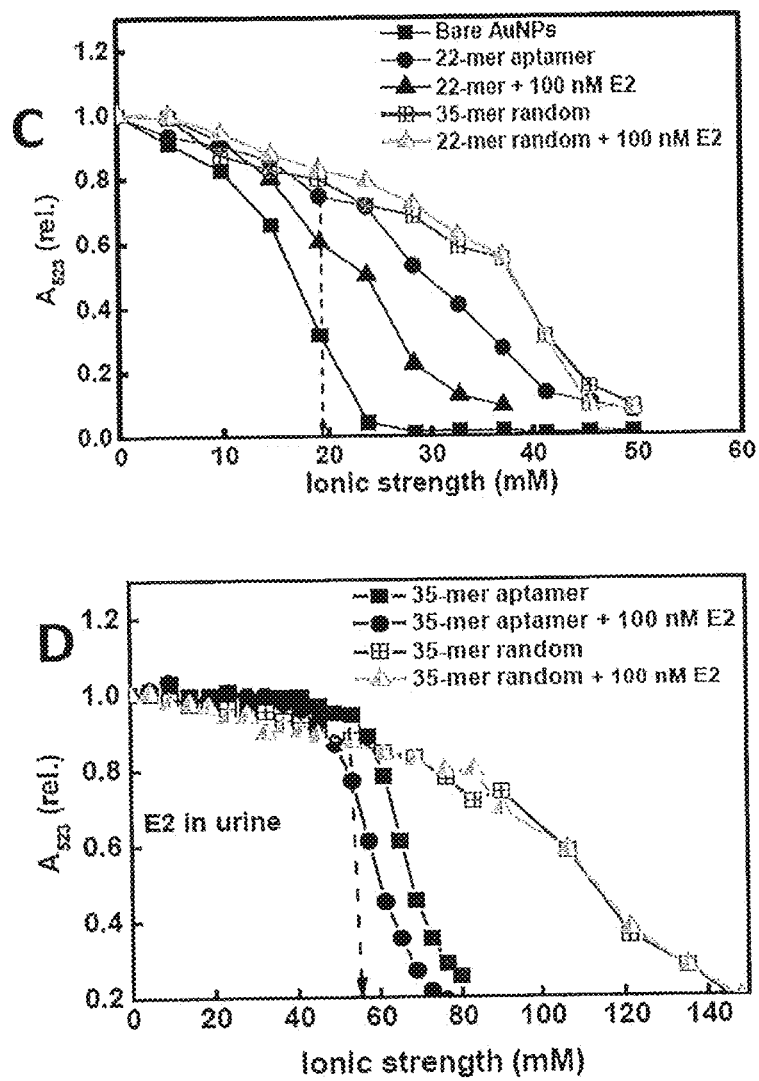
Figure 19:
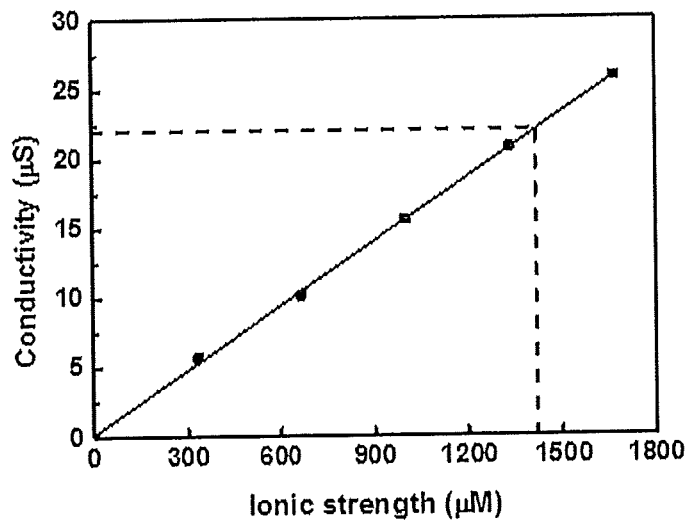
FIG. 19 shows Standard calibration curve of the conductivity of NaCl solutions to estimate the ionic strength of rat urine. 10 μL of the rat urine was diluted to 15 mL, using Milli-Q water, and the conductivity was measured. The final ionic strength of the rat urine sample is 2.1 mM; legend: - - - diluted rat's urine, ⎯ conductivity calibration curve using NaCl.
Figure 20:
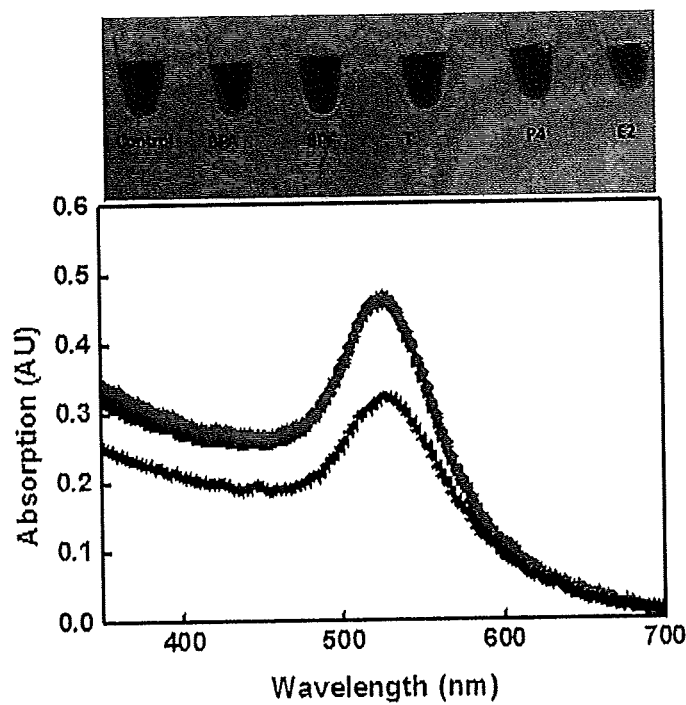
FIG. 20 shows a photograph (top) and UV-vis spectra of the specificity results using the 35-mer aptamer in rat urine samples spiked with 200 nM BPA, BPF, progesterone (P4) and testosterone (T), and E2; legend: ●-BPA, ■-control, ◄-E2, ▲-BPF, ▼-T, ♦-P4.
Figure 21:
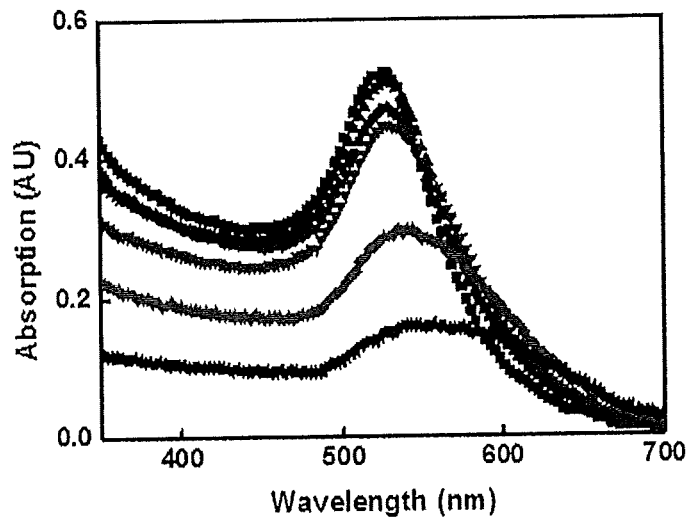
FIG. 21 shows the absorption spectra of E2 sensing in rat urine samples using the 75-mer aptamer; legend: ■-0 E2, ●-5 μM E2, ▲-15 μM E2, ▼-25 μM E2, ♦-35 μM E2, ◄-50 μM E2.
Figure 22:
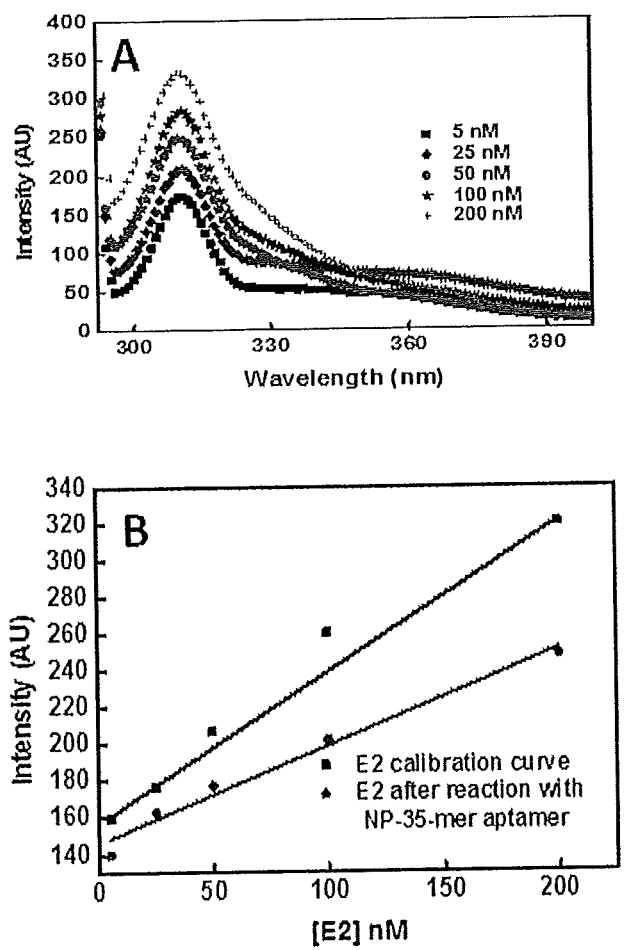
FIG. 22 shows determination of the dissociation constant (K$_D$) for the 35-mer aptamer. a) Representative emission spectra of E2 in BWB. b) Calibration curve of E2 and fluorescent intestines of E2 after reaction with NP-35-mer. c) Saturation binding curve of E2 with the NP-35-mer. Experimental data (from plotting normalised unbound fraction $f_a$ against E2 concentration) was fitted using a non-linear regression function as explained in the Methods section in the main text.
Figure 22:
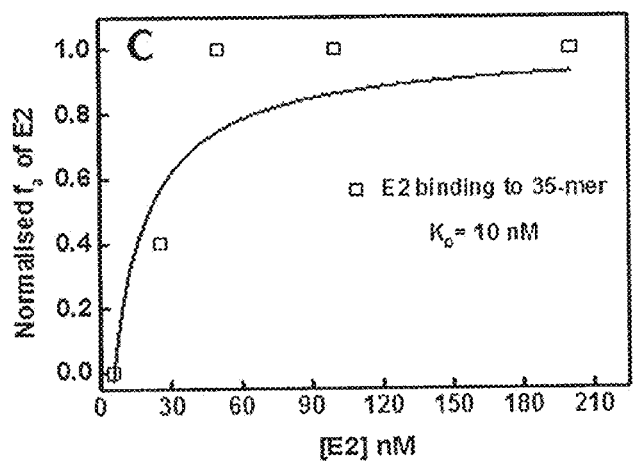
Figure 23:
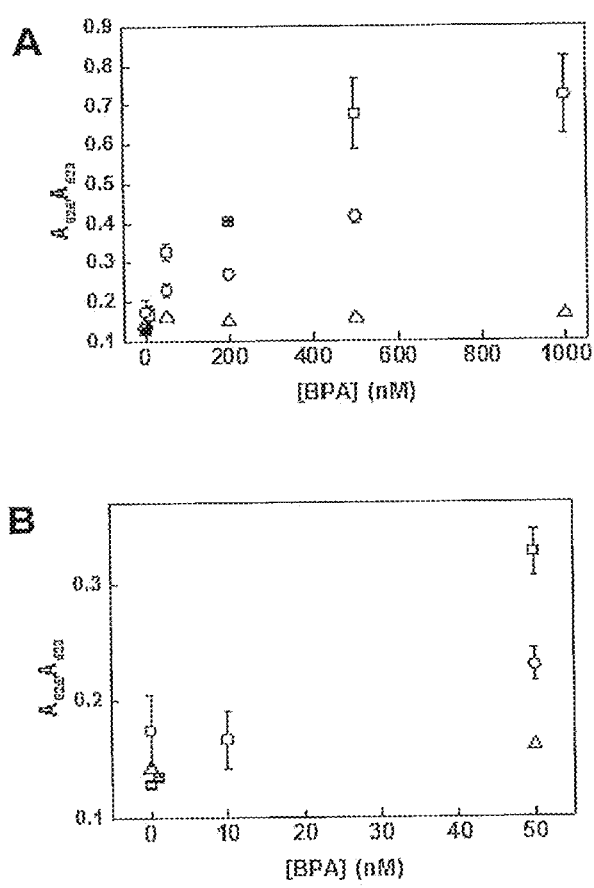
FIG. 23 shows a colorimetric response of aptamers selective for BPA. Error bars indicate standard deviation of the mean of three experiments. Legend—Δ: Random 75-mer DNA; ◯: 75-mer BRA aptamer; ☐: 42-mer BPA aptamer.
Figure 24:
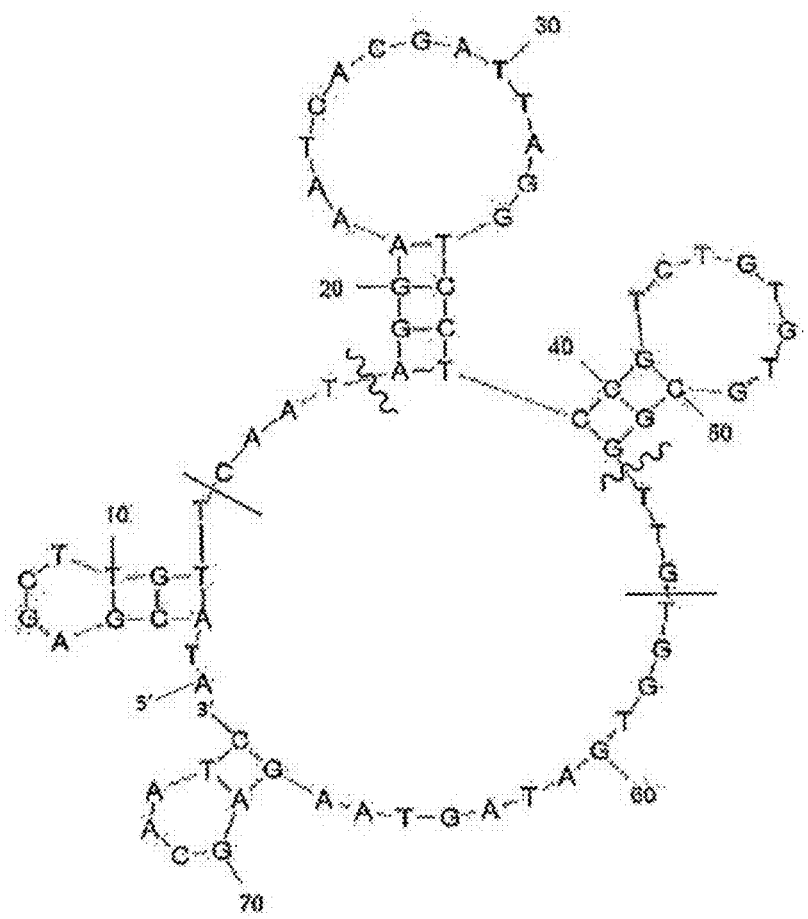
FIG. 24 shows the 2D structured of the 75-mer BPA aptamer. ∿∿ indicates estimated start and end points comprising central loop points of the ligand binding; — indicates the start and end points of the 42-mer BPA aptamer. The sequence shown in this Figure corresponds to SEQ ID NO: 1.

Procedure for Synthesis of AuNPs:

HAuCl$_4$ (100 mL, 1 mM) is reduced with sodium citrate (10 mL, 38.8 mM) to provide AuNPs of 10 nm diameter (FIG. 13). [Grabar, K. C., at al, *Anal. Chem.*, 1995, 67, 1217-1225]. An aqueous solution of HAuCl$_4$ (100 mL, 1 mM) is vigorously stirred at 250° C. for 10 min and a solution of sodium citrate (10 mL, 38.8 mM) is added at once. The solution is boiled for 10 minutes, and is stirred for another 15 minutes at room temperature. AuNPs solution is stored at 4° C. prior to use. The concentration of AuNPs is calculated according to the Beer-Lambert law, using an extinction coefficient of $2.7 \times 10^8$ M$^{-1}$ cm$^{-1}$ at 525 nm [Haiss, W., et al., *Anal. Chem.*, 2007, 79, 4215-21]. The concentration of the AuNPs is estimated to be 14 nM.

General Procedure for AuNP-Aptamer Blending and Coincubation:

Those of skill in the art will realise that the procedure for coating the NPs is a standard general procedure and can be applied to other NPs suitable for application with the invention. AuNPs are used for exemplification and the procedure is not restricted only to AuNPs.

AuNPs are purified by a 1:10 dilution of AuNPs in Milli-Q water, centrifugation at 12,500 rpm for 15 minutes (MIKRO 120-Hettich). The AuNPs are then re-suspended in Milli-Q water at the original 1:10 dilution. The removal of the excess citrate is confirmed by ζ-potential values of (−33.46 mV (±0.35)) before and (−23.5 mV (±0.28)) after purification. A 0.1 nmole solution of the aptamer in Milli-Q water, or poly-T in the case of control experiments, is prepared and immediately added to the purified AuNPs suspended in 0.3 mL of Milli-Q water, to provide an aptamer concentration of 33.3 nM for the E2 aptamers (SEQ ID Nos: 1, 2, 3, 4, 5, 6), and 100 nM for the BPA aptamers (SEQ ID Nos: 7 and 8), with a aptamer: particle number ratios of 3:1 and 9:1, respectively, for a particle number of $2.5 \times 10^{13}$. The NP-aptamer samples are prepared 1 hour prior to sensing experiments.

General Procedure for Salt Titration Experiments:

Those of skill in the art will realise that this procedure is a standard general procedure and can be applied to other NPs suitable for application with the invention. AuNPs are used for exemplification and the procedure is not restricted only to AuNPs.

Figure 1:
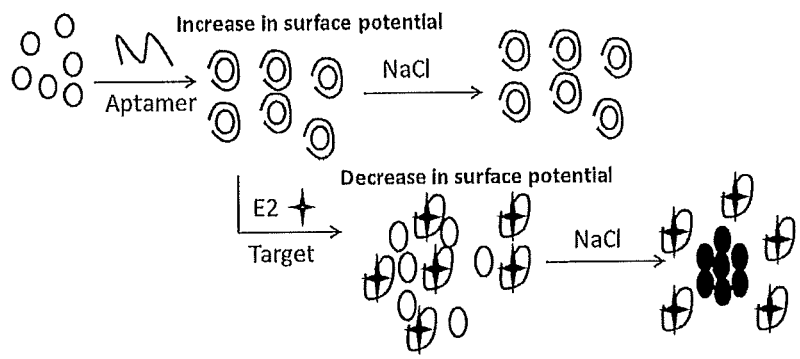
FIG. 1 (A) is a schematic depiction of aggregation in the colorimetric assay of E2;
  (B) Shows saturation binding curve of E2 with the NP-35-mer, NP-22-mer and NP-75-mer aptamers. Experimental data (from plotting normalised unbound fraction as 1/fa against 1/E2 concentration) was fitted using a linear regression function.
Figure 1:
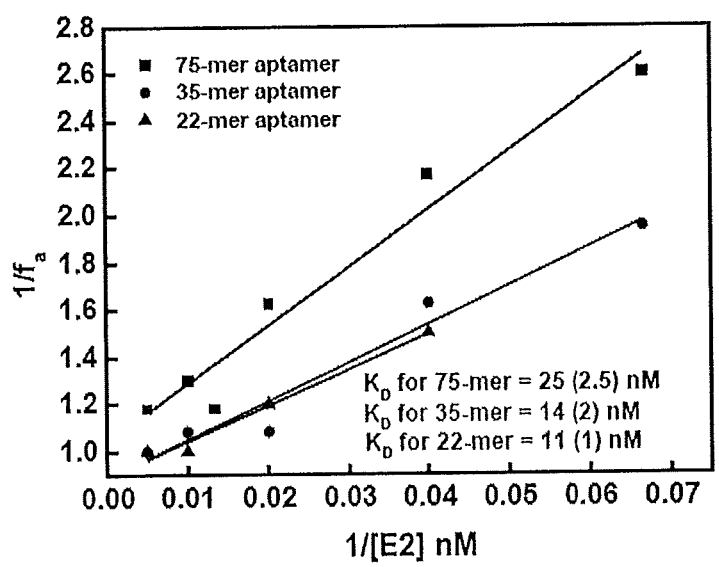
Figure 2:
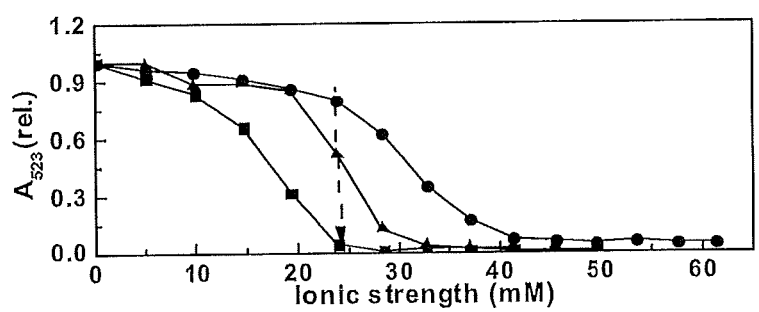
FIG. 2 shows determination of the optimal salt concentration (indicated by the dashed arrow) for signal generation by comparison between the salt dependent aggregation of AuNPs (■) AuNP-75-mer aptamer (●), and AuNP-75-mer aptamer in the presence of 100 nM E2 (▲). Aggregation is measured via the relative absorption at 523 nm as indicated in the inset.
Figure 3:
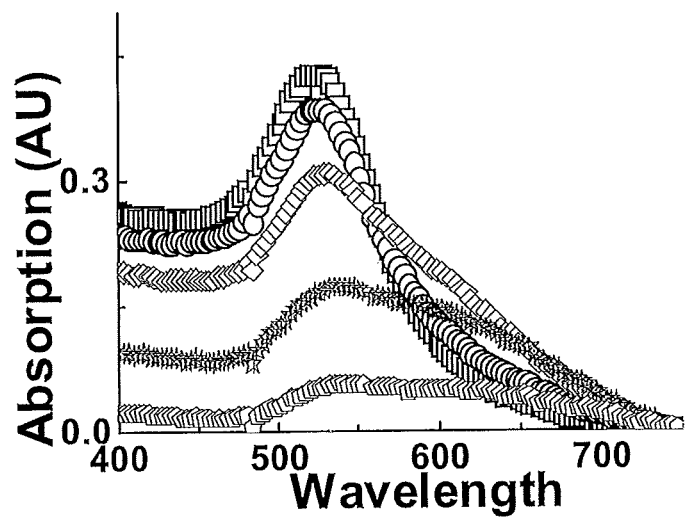
FIG. 3 shows raw UV-vis spectra for sensing E2 using the 75-mer aptamer, 0 nM (□), 5 nM (○), 100 nM (◇), 200 nM (☆) and 400 nM (⌂).
Figure 4:
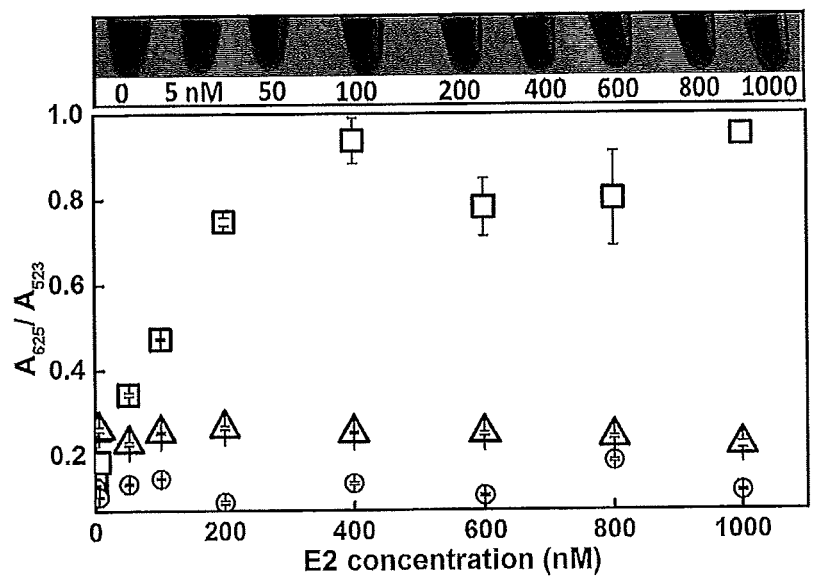
FIG. 4 shows colorimetric response towards a range of E2 concentrations for the AuNP-75-mer aptamer (□) when compared with bare AuNPs (○) and AuNP-poly-T controls (Δ). The colour change over the range is from pink/red colloidal solution to purple/blue. Error bars indicate standard deviation of the mean of three experiments.
Figure 5:
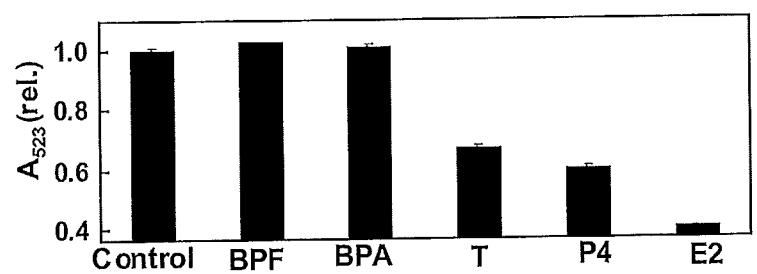
FIG. 5 shows specificity examination of the 75-mer aptamer towards a number of interfering targets at 200 nM concentration. Error bars indicate standard deviation of the mean of three experiments.
Figure 6:
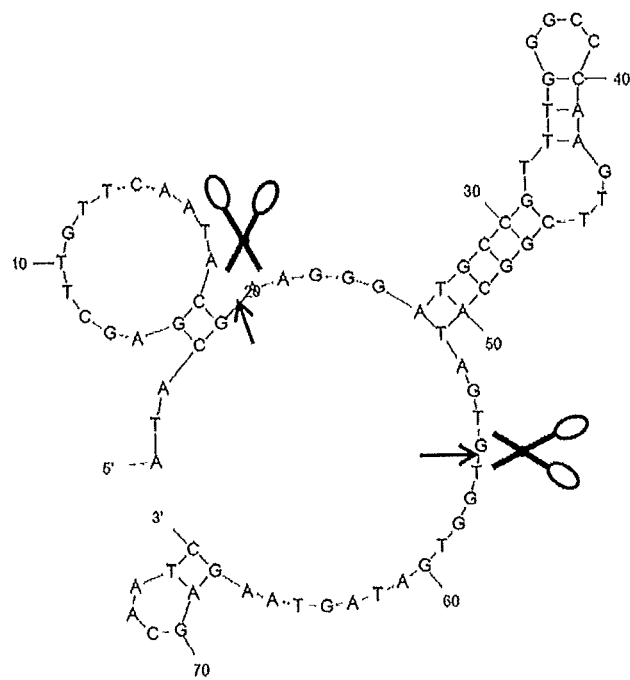
FIG. 6 Shows secondary structure of the 75-mer aptamer predicted by M-fold program indicating the truncation positions. The sequence shown in this Figure corresponds to SEQ ID NO: 1.
Figure 7:
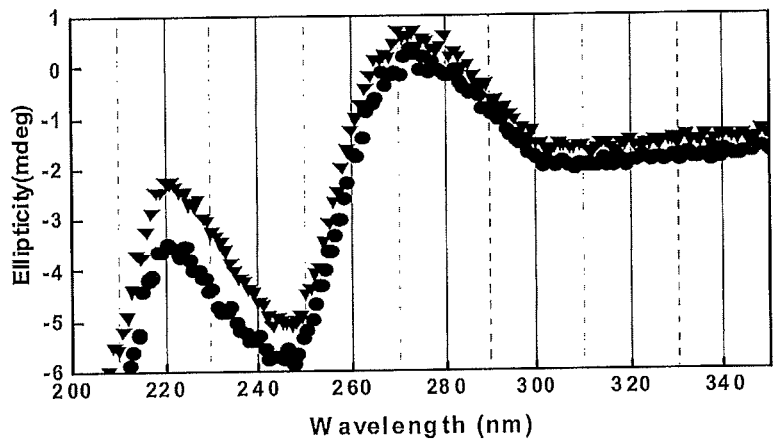
FIG. 7 shows CD spectra for 400 nM of the 75-mer incubated with 0 μM (●) E2 and 10 μM E2 (▲).
Figure 8:
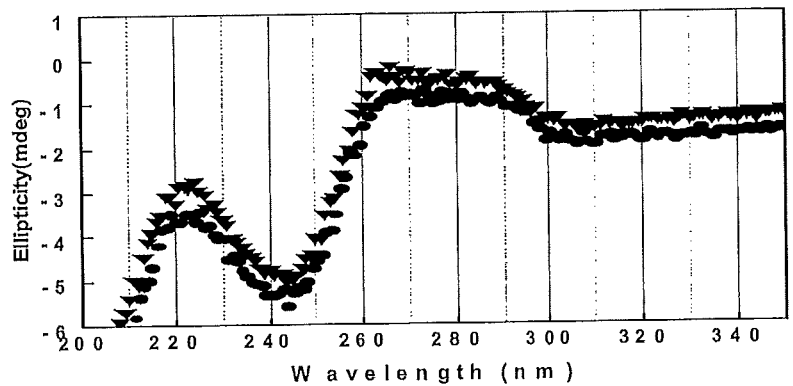
FIG. 8 shows CD spectra for 600 nM of the 35-mer aptamers, incubated with 0 μM E2 (●) and 10 μM E2 (▲).
Figure 9:
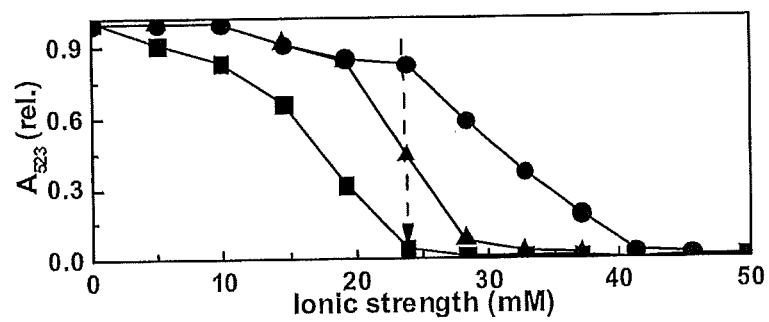
FIG. 9 shows determination of the optimal salt concentration, indicated by the dashed arrow at 24 mM, for signal generation comparison between the salt dependent aggregation of AuNPs (●), AuNP-35-mer aptamer (♦), and AuNP-35-mer aptamer in the presence of 100 nM E2 (▲).
Figure 10:
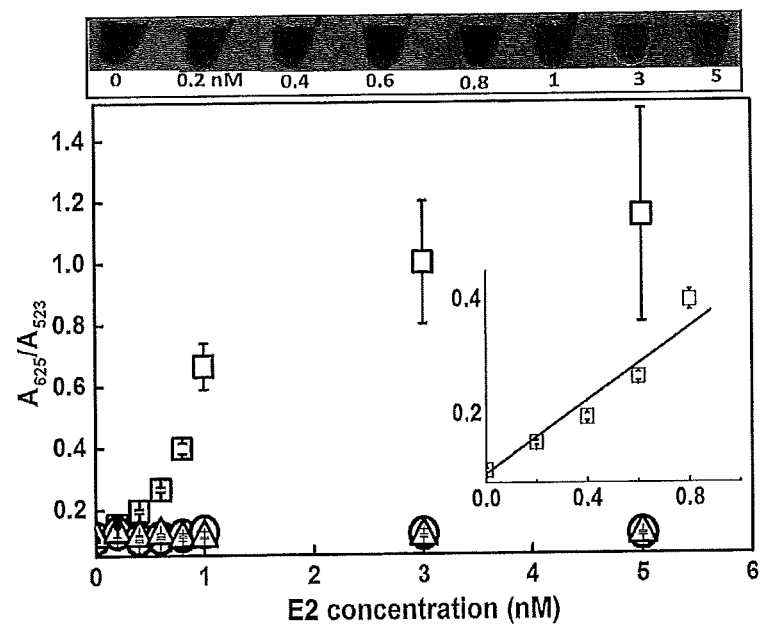
FIG. 10 shows colorimetric responses towards a range of E2 concentrations using the AuNP-35-mer aptamer (□) when compared with bare AuNPs (○) and AuNP-poly-T (Δ) controls (figure inset indicated an extended linear response of the same figure). Error bars indicate standard deviation of the mean of three experiments.
Figure 11:
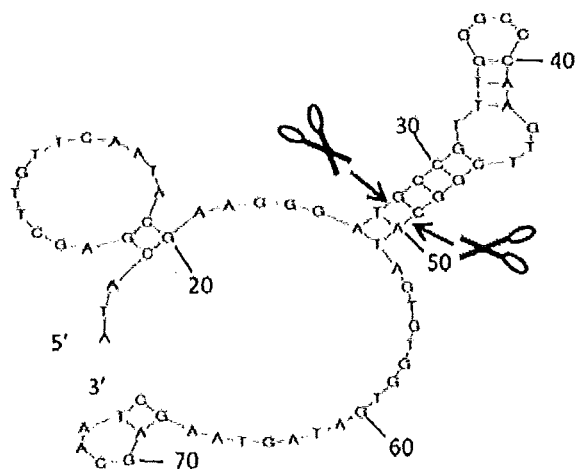
FIG. 11 (A) shows the calculated binding domain for the 22-mer E2 aptamer;
  (B) shows the data set for the 22-mer aptamer system compared with the bare NP and a random 22 aptamer the non-random 22-mer system delivers detection limits of around 200 pM. However, the magnitude of absorption change is reduced compared to the 35-mer aptamer. The sequence shown in this Figure corresponds to SEQ ID NO: 1.
Figure 11B:
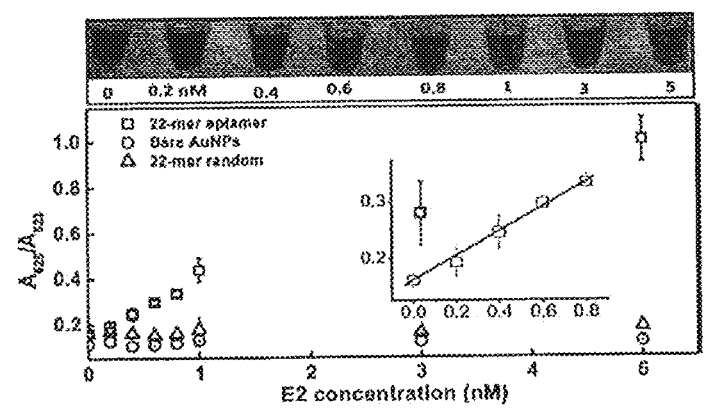
Figure 12:
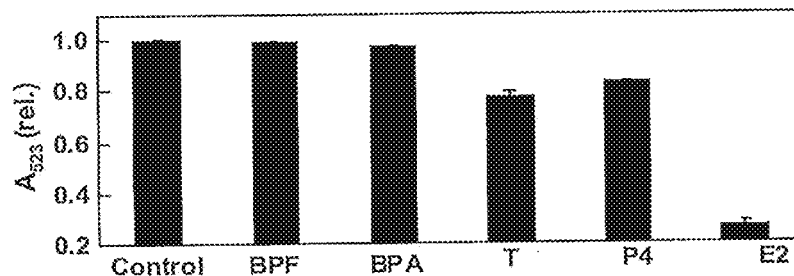
FIG. 12 Shows the selectivity of the AuNP-35-mer aptamer colloidal solution for target small molecules at 800 pm concentration. Error bars indicate standard deviation of the mean of three experiments.

The ionic strength of the aptamer solution is independently adjusted to the values stated in FIG. 9, by adding different volumes of 0.5 M NaCl to 100 μL samples of bare NPs, NP-aptamer, or NPs-aptamer+100 nM E2 or BPA. For example, the optimum ionic strength for the AuNP-75-mer E2 (SEQ ID No:1) and the AuNP-75-mer BPA (SEQ ID No:7) aptamer system is 23.8 mM. The optimum ionic strength for the AuNP-42-mer BPA aptamer (SEQ ID No:8) system is 14.5 mM The samples are allowed to stand for 15 minutes before measuring the degree of aggregation by UV-vis absorption at 523 nm.

General Procedure for $K_D$ Measurement:

The procedure for estimating the $K_D$ of the 35-mer was based on that used for the 75-mer [Alsager, O. A; Kumar, S.; Willmott, G. R.; McNatty, K. P.; Hodgkiss, J. M. Biosens. Bioelectron. 2014, 57C, 262]. The aptamer was immobilized on polystyrene nanoparticles, exposed to aliquots of E2, and the fraction bound E2 was measured via UV fluorescence and fit to a binding isotherm after separation of the nanoparticles from the supernatant. 200 nmol of EDC and NHS (20 μL of 0.01 M in MES) was added to activate 400 μL of carboxylate polystyrene nanoparticles (NPs, $5.2 \times 10^{10}$ particle mL$^{-1}$) in MES for 40 min, followed by addition of 0.1 nmol of 35-mer aptamer and incubation overnight. The samples were centrifuged at 14000 rpm for 30 min and the supernatant was discharged. 1 mL E2 with various concentrations in BWB containing 5% ethanol was added to the samples, sonicated for 10 mins, and incubated overnight. The samples were then centrifuged at 14000 rpm for 30 min, the supernatant was isolated, transferred to a 1 cm quartz cuvette, and the fluorescence of the unbound E2 was collected via 279 nm with a Shimadzu RF-5301PC spectrofluorophotometer. The measured fluorescence intensities at 310 nm were first converted to concentration via an E2 calibration curve. By expressing a measured E2 concentration as an unbound fraction, $f_a$, and plotting against total E2 concentration, the $K_D$ was determined as 10 nM by fitting to the binding isotherm in equation 1. We observed a saturation offset at $f_a$=0.6 due to partial loss of the NP-35-aptamer conjugate during the centrifugation, and renormalized to $f_a$ (max)=1.

$$f_a = \frac{[E2]}{K_D + [E2]} \quad (1)$$

Procedure for E2 Detection:

Those of skill in the art will realise that this procedure is a standard general procedure and can be applied to other NPs suitable for application with the invention. AuNPs are used for exemplification and the procedure is not intended to be restricted only to AuNPs.

Sample water is collected from the Hutt River, Wellington, New Zealand and pre-treated by stirring 50 mL overnight at room temperature with 1 g of activated charcoal and filtering twice through 0.22 μm syringe-filters to provide treated water. The conductivity of the treated water is measured as 100 μs cm$^{-1}$ (at 25° C. with the pH is 8) and indicates there is a very low salt concentration in the sample. Alternatively, Milli-Q water is used instead of treated river water.

Stock solutions of the target small molecules and/or other target substrate are made in ethanol before adding appropriate volumes to the treated water or Milli-Q water, and adjusting the final ethanol content to 5%, ensuring sufficient target small molecule and/or other target substrate solubility. 20 μL of the pre-treated test samples are added to 100 μL of AuNP-aptamer solution to obtain varying E2 concentrations and provide a total reaction volume of 120 μL.

Control samples are made up from blank water containing 5% ethanol. Samples are incubated for 10 minutes at room temperature to facilitate binding to the target. The optimised NaCl concentration determined from the salt titration experiments is added to the target detection solutions (10 mM for bare NPs, 23.8 mM for poly-T/E2 aptamer samples), followed by gentle shaking, The samples are visually inspected after 15 minutes, and the UV-vis absorption of 5 μL aliquots is measured using a Thermo Scientific NanoDrop™ 1000 Spectrophotometer.

Procedure for BPA Detection:

The same procedure outlined above for E2 detection was followed, but with the target substituted for BPA, and the aptamers substituted for BRA aptamers.

Animal Urine Study:

Rat urine is collected from sexually mature ship rats (*Rattus rattus*), filtered with 0.22 μm syringe-filters, and spiked with E2 and interfering molecules after adjusting the content of ethanol to 5% (control rat urine sample comprised blank rat urine containing 5% ethanol). 5 μL of spiked urine is added to 100 μL AuNP-poly-T, AuNP-75-mer aptamer or AuNP-35-mer aptamer, incubated at 50° C. for 10 min, followed by addition of optimised NaCl (57.4 mM), gentle shaking, visual inspection after 15 min and measurement of UV-vis absorption as described above.

ζ-Potential Measurements for Au Nanoparticles:

Those of skill in the art will realise that this procedure is a standard general procedure and can be applied to other NPs suitable for application with the invention. AuNPs are used for exemplification and the procedure is not restricted only to AuNPs.

120 μL samples of bare AuNPs, AuNP-aptamer, and AuNP-aptamer in the presence of 100 nM E2 in Milli-Q water, are incubated at room temperature for 1 hour and are centrifuged at 12,500 rpm for 15 minutes. The excess aptamer is removed by decantation of the supernatant and the NPs are re-suspended in 1 mL Milli-Q water. Samples are loaded in a folded capillary cell, inserted into a Zetasizer Nano ZS equipped with a 633 nm laser (Malvern Instruments, UK) and equilibrated at 25° C. for 2 minutes prior to measurement. Measurements are made in triplicate, with fixed parameters of pH 7, viscosity 0.887 mPa s, and refractive index of 1.33. The measurements are reported as average value±standard deviation (Table 2).

TABLE 2

ζ-Potential Values and Surface Densities for Different Samples Investigated during E2 Sensing

| sample | ζ-potential[a] | | a surface density[b] | |
| --- | --- | --- | --- | --- |
| | No E2 | 1 μM E2 | No E2 | 20 μM E2 |
| bare AuNPs | −23.5 (0.3) | −24.0 (0.7) | | |
| 75-mer aptamer | −40.2 (0.9) | −32.3 (0.9) | 1.12 | 0.48 |
| 75-mer random | −46.2 (0.7) | −47 (1) | 1.01 | 1.04 |
| 35-mer aptamer | −29 (1) | −25.0 (0.2) | 4.42 | 1.3 |
| 35-mer random | −41 (1) | −41.7 (0.3) | 4.08 | 3.4 |
| 22-mer aptamer | −29 (1) | −24.3 (0.8) | 4.2 | 2.1 |
| 22-mer random | −42 (2) | −38.0 (0.7) | 4.9 | 4.6 |

[a] mV (STD, n = 3).
[b] /10$^{13}$ molecule/cm$^2$.

CD Studies:

1 mL solutions of the 75-mer and 35-mer and 22-mer aptamers at 400 nM, 600 nM and 600 nM, respectively, are prepared in water containing 5% ethanol, 23.8 mM NaCl, and 0 or 10 μM of E2. Samples are measured in a 1 cm path length quartz cell. CD spectra are measured using a Chirascan CD spectrometer instrument over the wavelength range from 200 to 400 nm, scanned at 200 nm per minute.

INDUSTRIAL APPLICATION

The present invention provides useful methodology for the detection of target substrates in samples. The present invention may find use is the field of environmental, forensic, diagnostic testing of samples.

REFERENCES

Alsager, O. A, Kumar, S., Willmott, G. R., McNatty, K. P., Hodgkiss, J. M., 2014. Biosens. Bioelectron. 57C, 262-268.
Blackwell T K & Weintraub H (1990) Differences and similarities in DNA-binding preferences of MyoD and E2A protein complexes revealed by binding site selection. Science 250:1104-1110
Brown, K. A., Park, S., Hamad-Schifferli, K., 2008. J. Phys. Chem. C 112, 7517-7521.
Campbell, C. G., Borglin, S. E., Green, F. B., Grayson, A., Wozei, E., Stringfellow, W. T., 2006. Chemosphere 65, 1265-80.
Cekan, P., Jonsson, E. O., Sigurdsson, S. T., 2009. Nucleic Acids Res. 37, 3990-5.
Cruz-Aguado, J. a, Penner, G., 2008. J. Agric. Food Chem. 56, 10456-61.
Ellington, A. D., Szostak, J. W., 1990. Nature 346, 818-22.
Ge, J., Xing, W., Xue, X., Liu, C., Lu, T., Liao, J., 2007. J. Phys. Chem. C 111, 17305-17310.
Geyer, H. J., Rimkus, G. G., Scheunert, I., Kaune, A., Kettrup, K. S. A., G, M. Z. D. C., Larry, M., Donald, G. H., 2000. Bioaccumulation—New Aspects and Developments. Springer-Verlag, Berlin/Heidelberg.
Grabar, K. C., Freeman, R. G., Hommer, M. B., Natan, M. J., 1995. Anal. Chem. 67, 1217-1225.
Haiss, W., Thanh, N. T. K., Aveyard, J., Fernig, D. G., 2007. Anal. Chem. 79, 4215-21.
He, J., Liu, Y., Fan, M., Liu, X., 2011. J. Agric. Food Chem. 59, 1582-6.
Huizenga, D. E., Szostak, J. W., 1995. Biochemistry 34, 656-65.
Jana, N. R., Gearheart, L., Murphy, C. J., 2001. Adv. Mater. 13, 1389-1393.

Jin, R., Wu, G., Li, Z., Mirkin, C. A., Schatz, G. C., 2003. J. Am. Chem. Soc. 125, 1643-54.
Jo, M., Ahn, J.-Y., Lee, J., Lee, S., Hong, S. W., Yoo, J.-W., Kang, J., Dua, P., Lee, D.-K., Hong, S., Kim, S., 2011. Oligonucleotides 21, 85-91.
Karsisiotis, A. I., Hessari, N. M., Novellino, E., Spada, G. P., Randazzo, A., Webba da Silva, M., 2011. Angew. Chem. Int. Ed. Engl. 50, 10645-8.
Kim, Y. S., Jung, H. S., Matsuura, T., Lee, H. Y., Kawai, T., Gu, M. B., 2007. Biosens. Bioelectron. 22, 2525-31.
Kim, Y. S., Kim, J. H., Kim, I. A., Lee, S. J., Jurng, J., Gu, M. B., 2010. Bioelectron. 26, 1644-9.
Li, H., Rothberg, L., 2004. Proc. Natl. Acad. Sci. U.S.A. 101, 14036-9.
McKeague, M., Derosa, M. C., 2012. J. Nucleic Acids 2012, 748913.
McManus, S. a, Li, Y., 2013. PLoS One 8, e64131.
Mei, Z., Chu, H., Chen, W., Xue, F., Liu, J., Xu, H., Zhang, R., Zheng, L., 2013. Biosens. Bioelectron, 39, 26-30.
Nonaka, Y., Sode, K., Ikebukuro, K., 2010. Molecules 15, 215-25.
Redel, E., Krämer, J., Thomann, R., Janiak, C., 2009. J. Organomet. Chem. 694, 1069-1075.
Shi, H., Zhao, G., Liu, M., Fan, L., Cao, T., 2013, J. Hazard. Mater. 260, 754-761.
Song, K.-M., Cho, M., Jo, H., Min, K., Jeon, S. H., Kim, T., Han, M. S., Ku, J. K., Ban, C., 2011. Anal. Biochem. 415, 175-81.
Stoltenburg, R., Reinemann, C., Strehlitz, B., 2007. Biomol. Eng. 24, 381-403.
Teranishi, T., Hosoe, M., Tanaka, T., Miyake, M., 1999. J. Phys. Chem. B 103, 3818-3827.
Tuerk, C., Gold, L., 1990, Science (80), 249, 505-510.
Vorlíčková, M., Kejnovská, I., Bednářová, K., Renčiuk, D., Kypr, J., 2012. Chirality 24, 691-8.
Wu, J., Chu, H., Mel, Z., Deng, Y., Xue, F., Zheng, L., Chen, W., 2012. Anal. Chim. Acta 753, 27-31.
Wu, S.-H., Chen, D.-H., 2004. J. Colloid Interface Sci. 273, 165-9.
Xue, F., Wu, J., Chu, H., Mei, Z., Ye, Y., Liu, J., Zhang, R., Peng, C., Zheng, L., Chen, W., 2012. Microchim. Acta 180, 109-115.
Yang, C., Wang, Y., Marty, J.-L., Yang, X., 2011. Biosens. Bioelectron. 26, 2724-7.
Yin, Y., Li, Z.-Y., Zhong, Z., Gates, B., Xia, Y., Venkateswaran, S., 2002. J. Mater. Chem. 12, 522-527.
Zhao, W., Brook, M. a, Li, Y., 2008. Chembiochem 9, 2363-71.
Zheng, Y., Wang, Y., Yang, X., 2011. Sensors Actuators B Chem. 156, 95-99.

The invention claimed is:

1. A method for selecting an aptamer for use in a particle detection assay, the method comprising:
   (i) providing a plurality of aptamers, wherein each aptamer comprises:
      (a) a ligand binding domain selective for a target substrate; and
      (b) at least one non-ligand binding domain comprising one or more nucleotides,
         wherein the at least one non-ligand binding domain promotes a direct association between the aptamer and a particle; and
         wherein each aptamer differs only in the number and sequence composition of the non-ligand binding domain nucleotides;
   (ii) associating each aptamer with a particle to form a non-covalent aptamer-particle complex in the absence of the target substrate;
   (iii) incubating the aptamer-particle complex with a target substrate in the presence of salt, wherein the aptamer dissociates from the particle when binding to the target substrate;
   (iv) measuring a signal transduction produced in step (iii) in the particle detection assay; and
   (v) selecting an aptamer which generates an optimized signal transduction measured in step (iv) when compared to the signal transduction generated by the other aptamers from the plurality of aptamers tested.

2. The method according to claim 1, wherein the non-ligand binding domain is located at the 5' end, the 3' end, or both the 5' and 3' ends of the ligand binding domain.

3. The method according to claim 1, wherein the non-ligand binding domain comprises 1 to 10 nucleotides.

4. The method according to claim 1, wherein the aptamer is an ssDNA or an RNA molecule.

5. The method according to claim 1, wherein the particle is a nanoparticle, microparticle, or quantum dot.

6. The method according to claim 1, wherein the assay is a colorimetric assay.

* * * * *

SEQUENCE LISTING

<160> NUMBER OF SEQ ID NOS: 8

<210> SEQ ID NO 1
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 1
atacgagctt gttcaatacg aagggatgcc gtttgggccc aagttcggca tagtgtggtg    60
atagtaagag caatc    75

<210> SEQ ID NO 2
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 2
aagggatgcc gtttgggccc aagttcggca tagtg    35

<210> SEQ ID NO 3
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 3
gccgtttggg cccaagttcg gc    22

<210> SEQ ID NO 4
<211> LENGTH: 75
<212> TYPE: DNA
<213> ORGANISM: Artificial Sequence
<220> FEATURE:
<223> OTHER INFORMATION: Synthetic Polynucleotide

```
<400> SEQUENCE: 4
aggcctaagg gcataattag ctcgagctcg aaaggggtta tatgatgatt tgaattcatg        60
gggcccgact cggat                                                         75

<210> SEQ ID NO 5
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 5
acgggtggcc gccaggtctt gaagtggcag tatta                                   35

<210> SEQ ID NO 6
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 6
tgggcccttt acggaccgcg tg                                                 22

<210> SEQ ID NO 7
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 7
atacgagctt gttcaatagg aaatcacgat taggtcctcc gtctgtgtgc ggttgtggtg        60
atagtaagag caatc                                                         75

<210> SEQ ID NO 8
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 8
caataggaaa tcacgattag gtcctccgtc tgtgtgcggt tg                           42
```